(12) United States Patent
Ono et al.

(10) Patent No.: US 8,048,898 B2
(45) Date of Patent: Nov. 1, 2011

(54) INHIBITOR OF BINDING OF S1P$_1$

(75) Inventors: Naoya Ono, Toshima-ku (JP); Fumiyasu Shiozawa, Toshima-ku (JP); Tetsuya Yabuuchi, Toshima-ku (JP); Hironori Katakai, Toshima-ku (JP)

(73) Assignee: Taisho Pharmaceutical Co., Ltd, Tokyo (JP)

(*) Notice: Subject to any disclaimer, the term of this patent is extended or adjusted under 35 U.S.C. 154(b) by 0 days.

(21) Appl. No.: 12/671,401

(22) PCT Filed: Aug. 1, 2008

(86) PCT No.: PCT/JP2008/063851
§ 371 (c)(1),
(2), (4) Date: Jan. 29, 2010

(87) PCT Pub. No.: WO2009/017219
PCT Pub. Date: Feb. 5, 2009

(65) Prior Publication Data
US 2010/0234594 A1    Sep. 16, 2010

(30) Foreign Application Priority Data
Aug. 1, 2007 (JP) ................. 2007-201274

(51) Int. Cl.
| C07D 413/14 | (2006.01) |
| C07D 413/12 | (2006.01) |
| C07D 401/14 | (2006.01) |
| C07D 401/12 | (2006.01) |
| C07D 213/70 | (2006.01) |
| C07D 213/68 | (2006.01) |
| C07D 213/643 | (2006.01) |
| A61K 31/5377 | (2006.01) |
| A61K 31/496 | (2006.01) |
| A61K 31/4725 | (2006.01) |
| A61K 31/4709 | (2006.01) |
| A61K 31/4439 | (2006.01) |
| A61K 31/4436 | (2006.01) |
| A61K 31/443 | (2006.01) |
| A61K 31/44 | (2006.01) |

(52) U.S. Cl. ............... 514/351; 514/253.12; 514/235.5; 514/307; 514/314; 546/300; 546/148; 546/167; 544/365; 544/124; 544/131

(58) Field of Classification Search ............ 514/253.12, 514/235.5, 307, 314, 351; 544/360, 365, 544/124, 131; 546/300, 148, 167
See application file for complete search history.

(56) References Cited

U.S. PATENT DOCUMENTS

| 5,516,783 A * | 5/1996 | Whittaker et al. ........... 514/303 |
| 5,910,506 A | 6/1999 | Sugimoto et al. |
| 2003/0229125 A1 | 12/2003 | Haaf et al. |
| 2005/0124654 A1 * | 6/2005 | Groneberg et al. ........... 514/313 |
| 2007/0232682 A1 | 10/2007 | Beard et al. |
| 2009/0131438 A1 | 5/2009 | Ono et al. |
| 2010/0041655 A1 | 2/2010 | Ono et al. |

FOREIGN PATENT DOCUMENTS

| EP | 0786455 A1 | 7/1997 |
| EP | 1798226 A1 | 6/2007 |
| JP | 5-194412 A | 8/1993 |
| JP | 2002-212070 A | 7/2002 |
| JP | 2002-332278 A | 11/2002 |
| JP | 2003-137894 A | 5/2003 |
| JP | 2003/530388 A | 10/2003 |
| JP | 2004/532276 A | 10/2004 |

(Continued)

OTHER PUBLICATIONS

Extended European Search Report issued Nov. 23, 2010 from the European Patent Office in a counterpart European Application No. 07713881.6 of the co-pending U.S. Appl. No. 12/278,477.

(Continued)

*Primary Examiner* — Joseph Kosack
*Assistant Examiner* — Matthew Coughlin
(74) *Attorney, Agent, or Firm* — Sughrue Mion, PLLC

(57) ABSTRACT

A compound represented by formula (I) or a pharmaceutically acceptable salt thereof:

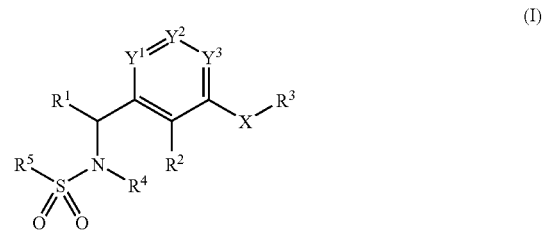

(wherein $Y^1$ represents a nitrogen atom or a group represented by $CR^A$, $Y^2$ represents a nitrogen atom or a group represented by $CR^B$, $Y^3$ represents a nitrogen atom or a group represented by $CR^C$, $R^A$, $R^B$ and $R^C$, which may be the same or different, each represent a hydrogen atom, etc. (excluding the case where $Y^1$ is $CR^A$, $Y^2$ is $CR^B$ and $Y^3$ is $CR^C$), X represents an oxygen atom, etc., $R^1$ represents a $C_1$-$C_6$ alkyl group, etc., $R^2$ represents a $C_1$-$C_6$ alkyl group, etc., $R^3$ represents an optionally substituted phenyl group, etc., $R^4$ represents a hydrogen atom, etc., and $R^5$ represents an optionally substituted phenyl group, etc.) has an inhibitory effect on the binding between S1P and its receptor Edg-1(S1P$_1$), and is useful as a therapeutic agent for autoimmune diseases, rheumatoid arthritis, asthma, atopic dermatitis, rejection after organ transplantation, cancer, retinopathy, psoriasis, osteoarthritis, or age-related macular degeneration, etc.

15 Claims, No Drawings

FOREIGN PATENT DOCUMENTS

| WO | 96/10019 A1 | 4/1996 |
|---|---|---|
| WO | 01/77089 A1 | 10/2001 |
| WO | 02/18395 A1 | 3/2002 |
| WO | 02/100853 A1 | 12/2002 |
| WO | 03/000679 A2 | 1/2003 |
| WO | 03/073986 A2 | 9/2003 |
| WO | 03/074008 A2 | 9/2003 |
| WO | 03/097028 A1 | 11/2003 |
| WO | 03/105771 A2 | 12/2003 |
| WO | 2004/024673 A1 | 3/2004 |
| WO | 2004/074257 A1 | 9/2004 |
| WO | 2004/089367 A1 | 10/2004 |
| WO | 2004/103279 A2 | 12/2004 |
| WO | 2005/123677 A1 | 12/2005 |
| WO | 2006/013948 A1 | 2/2006 |
| WO | 2006/097489 A1 | 9/2006 |
| WO | WO 2006097489 A1 * | 9/2006 |
| WO | 2007/083089 A1 | 7/2007 |
| WO | 2007/091570 A1 | 8/2007 |
| WO | 2007/112322 A2 | 10/2007 |
| WO | 2007/122401 A1 | 11/2007 |
| WO | 2007/129019 A1 | 11/2007 |

OTHER PUBLICATIONS

Gehlen, H., et al., '2-Amino-1,3,4-oxadiazoles. IX. Oxidation of Aldehyde Semicarbazones to 2-amino-1, 3,4-oxadiazoles and Their Conversion Into 1-acylsemicarbazides, Justus Liebigs Annalen Der Chemi, vol. 651, pp. 133-136, 1962.

International Search Report for International Application No. PCT/JP2008/063851, dated Sep. 22, 2008.

Gehlen et al., "2-Amino-1,3,4-oxadiazoles. VIII. Formation of 2-amino-5-aminoalkyl-1,3,4-oxadiazoles and their conversion into 1,2,4-triazoles and triazolones", Justus Liebigs Annalen der Chemie, Paedagogischen Hochschule, English language STN Abstract, vol. 651, pp. 128-132, 1962.

Von Heinz Gehlen, et al; Zur Kenntnis der 2-Amino-1,3,4-oxdiazole, X, "3-Alkoxy-1,2,4-Triazole Durch Alkoholyse von 2-Amino-1,3,4-Oxdiazolen", Liebigs Ann. Chem., vol. 651, pp. 137-141 (with an English translation), 1962.

M. Germana Sanna et al., "Sphingosine 1-Phosphate (S1P) Receptor Subtypes $S1P_1$ and $S1P_3$, Respectively, Regulate Lymphocyte Recirculation and Heart Rate", The Journal of Biological Chemistry, vol. 279, No. 14, Issue of Apr. 2, pp. 13839-13848, 2004.

Jeremy J. Clemens et al., "Synthesis of Para-Alkyl Aryl Amide Analogues of Sphingosine-1-phosphate: Discovery of Potent S1P Receptor Agonists", Bioorganic & Medicinal Chemistry Letters, vol. 13, pp. 3401-3404, 2003.

Guofeng Jia, et al., "Syntheses of Some New 4-Amino-5-(N-methyl-arylsulfonamido)methyl-1,2,4-triazole-3-thiones and Their Derivatives", Heteroatom Chemistry, vol. 7, No. 4, pp. 263-267, 1996.

Supplemental European Search Report dated Oct. 13, 2009, issued in European Application No. 07708069.5.

James R. Van Brocklyn et al., Sphingosine-1-phosphate stimulates motility and invasiveness of human glioblastoma multiforme cells, Cancer Letters, Elsevier, 2003, pp. 53-60, vol. 199.

Zdzislaw Brzozowski, 2-Mercapto-N-(Azolyl) Benzenesulphonamides I. Synthesis of N-(1,1-Dioxo-1,4,2-Benzodithianzin-3-YL)Guanidines and Their Transformations Into 2-Mercapto-N-(5-Amino-1,2,4-Triazol-3-YL) Benzenesulphonamide Dervatives with Potential Anti-HIV or Anticancer Activity, Department of Drug Technology, Faculty of Pharmacy, School of Medicine, Acta Poloniae Pharmaceutica-Drug Research, Polish Pharmaceutical Society, 1995, pp. 91-101, vol. 52, No. 2.

Timothy Hla, Physiological and Pathological Actions of Sphingosine 1-Phosphate, 15 Sem. Cell & Dev. Bio., 513 (2004).

* cited by examiner

INHIBITOR OF BINDING OF $S1P_1$

CROSS REFERENCE TO RELATED APPLICATION

This application is a National Stage of International Application No. PCT/JP2008/063851, filed Aug. 1, 2008, which claims priority from Japanese Patent Application No. 2007-201274, filed Aug. 1, 2007, the contents of all of which are incorporated herein by reference in their entirety.

TECHNICAL FIELD

The present invention relates to novel compounds which have an inhibitory effect on the binding between sphingosine-1-phosphate having various physiological actions and its receptor Edg-1 (Endothelial differentiation gene receptor type-1, $S1P_1$), and also relates to pharmaceutical preparations comprising these compounds as active ingredients.

BACKGROUND ART

Sphingosine-1-phosphate (hereinafter referred to as "SIP") is a physiologically active lipid which is generated when sphingolipids (typified by sphingomyelin) are metabolized in cells. S1P is known to have a wide variety of actions such as cell differentiation induction, cell growth stimulation, cell motility control and apoptosis inhibition, and is also known to show physiological actions such as angiogenesis, bradycardia induction, inflammatory cell activation and platelet activation (Non-patent Document 1).

As SIP receptors, the following 5 subtypes have been reported: Edg-1($S1P_1$), Edg-3($S1P_3$), Edg-5($S1P_2$), Edg-6 ($S1P_4$) and Edg-8($S1P_5$) (Non-patent Document 2).

Among these subtypes, Edg-1($S1P_1$) is highly expressed in immunocytes (e.g., T cells, dendritic cells) and vascular endothelial cells, suggesting that Edg-1($S1P_1$) contributes deeply to S1P-stimulated T cell migration (Non-patent Document 3), mast cell migration (Non-patent Document 4), T and B cell egress from lymphoid organs (Non-patent Document 5) and angiogenesis (Non-patent Document 6), and is involved in autoimmune diseases such as Crohn's disease, irritable bowel syndrome, Sjogren's syndrome, multiple sclerosis and systemic lupus erythematosus, as well as other diseases such as rheumatoid arthritis, asthma, atopic dermatitis, rejection after organ transplantation, cancer, retinopathy, psoriasis, osteoarthritis, age-related macular degeneration, etc.

Thus, ligands for Edg-1($S1P_1$) would be effective for treatment or prevention of these diseases.

Edg-1($S1P_1$) ligands previously known include certain types of thiophene derivatives (Non-patent Document 7), phosphoric acid derivatives (Patent Documents 1 and 2, Non-patent Documents 8 and 9) and thiazolidine derivatives (Patent Document 3), carboxylic acid derivatives (Patent Documents 4, 5, 6 and 8, Non-patent Documents 10 and 11), amino group-containing derivatives (Patent Document 7), pyrrole derivatives (Patent Document 9), and triazole derivatives (Patent Documents 10 and 11).

Patent Document 1: WO2002/18395
Patent Document 2: JP 2003-137894 A
Patent Document 3: JP 2002-332278 A
Patent Document 4: WO2002/092068
Patent Document 5: WO2003/105771
Patent Document 6: WO2004/058149
Patent Document 7: WO2004/103279
Patent Document 8: WO2005/058848
Patent Document 9: WO2005/123677
Patent Document 10: WO2006/013948
Patent Document 11: WO2007/083089
Non-patent Document 1: J Biol. Chem. 2004, 279: 20555, FASEB J 2002, 16: 625, Proceedings of the Japanese Society for Immunology 2003, 33: 2-J-W30-20-P
Non-patent Document 2: Pharmacol Res 2003, 47: 401
Non-patent Document 3: FASEB J 2002, 16:1874
Non-patent Document 4: J Exp Med 2004, 199: 959
Non-patent Document 5: Nature 2004, 427: 355
Non-patent Document 6: J Clin Invest 2000, 106: 951, Biocchim Biophys Acta 2002, 1582: 222
Non-patent Document 7: J Biol Chem 2004, 279: 13839
Non-patent Document 8: Bioorg Med Chem Lett 2003, 13: 3401
Non-patent Document 9: J Biol. Chem. 2005; 280: 9833
Non-patent Document 10: J Med. Chem. 2004, 47: 6662
Non-patent Document 11: J Med. Chem. 2005, 48: 6169

DISCLOSURE OF THE INVENTION

Problems to be Solved by the Invention

The object of the present invention is to provide compounds having a novel skeleton, which have an inhibitory effect on the binding between S1P and its receptor Edg-1 ($S1P_1$) and which are useful for pharmaceutical purposes.

Means for Solving the Problems

As a result of extensive and intensive efforts made to find ligand compounds for Edg-1($S1P_1$), the inventors of the present invention have found that this object is achieved by a compound of the following formula (I) or a pharmaceutically acceptable salt thereof. This finding led to the completion of the present invention.

Embodiments will be given below for a compound of formula (I) (hereinafter each referred to as "the compound of the present invention").

(1)
A compound represented by formula (I) or a pharmaceutically acceptable salt thereof:

[Formula 1]

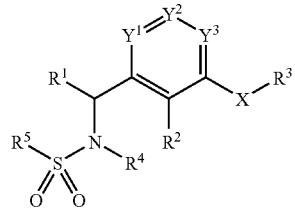

(I)

{wherein $Y^1$ represents a nitrogen atom or a group represented by $CR^A$, $Y^2$ represents a nitrogen atom or a group represented by $CR^B$, $Y^3$ represents a nitrogen atom or a group represented by $CR^C$, $R^A$, $R^B$ and $R^C$, which may be the same or different, each represent a hydrogen atom or a $C_1$-$C_6$ alkyl group (excluding the case where $Y^1$ is $CR^A$, $Y^2$ is $CR^B$ and $Y^3$ is $CR^C$), X represents an oxygen atom, a sulfur atom, a group represented by the formula —SO—, a group represented by the formula —$SO_2$—, or a group represented by the formula —$NR^6$— (wherein $R^6$ represents a hydrogen atom or a $C_1$-$C_6$ alkyl group), $R^1$ represents a hydrogen atom, a $C_1$-$C_6$ alkyl group, or a benzyl group, $R^2$ represents a hydrogen atom, a $C_1$-$C_6$ alkyl group, or a $C_3$-$C_8$ cycloalkyl group, $R^3$ represents (i) a $C_1$-$C_6$ alkyl group which may be substituted with 1 to 3 substituents selected from the group A [wherein the group A consists of a halogen atom, a phenyl group, a $C_1$-$C_6$ alkoxy group, an amino group which may be substituted with one or two $C_1$-$C_6$ alkyl groups, a morpholino group, and a piperazino group which may be substituted with a $C_1$-$C_6$ alkyl group(s)], (ii) a $C_3$-$C_8$ cycloalkyl group, or (iii) a phenyl group, a naphthyl group or an isoquinolinyl group, each of which may be substituted with 1 to 3 substituents selected from the group B [wherein the group B consists of a halogen atom, a $C_1$-$C_6$ alkyl group, a $C_1$-$C_6$ alkoxy group, an amino group which may be substituted with one or two $C_1$-$C_6$ alkyl groups, a morpholino group, a piperazino group which may be substituted with a $C_1$-$C_6$ alkyl group(s), a $C_1$-$C_6$ alkanoylamino group, and a $C_1$-$C_6$ alkylsulfonylamino group], $R^4$ represents a hydrogen atom or a $C_1$-$C_6$ alkyl group, and $R^5$ represents a phenyl group, a thienyl group, a thiazolyl group, a pyridyl group, a naphthyl group, an indanyl group, a dihydrobenzofuranyl group, a benzodioxolyl group, a benzothiadiazolyl group, a benzothienyl group or a quinolinyl group, each of which may be substituted with 1 to 5 substituents selected from the group C [wherein the group C consists of a $C_1$-$C_6$ alkyl group, a halogen atom, a trifluoromethyl group, a $C_1$-$C_6$ alkoxy group, a trifluoromethoxy group, a nitro group, a cyano group, and a $C_2$-$C_7$ alkanoyl group], or a $C_2$-$C_8$ alkenyl group which may be substituted with a phenyl group(s)}.

(2)

The compound or pharmaceutically acceptable salt thereof according to (1) above, wherein in formula (I), $Y^1$ is a nitrogen atom or CH, $Y^2$ is $CR^B$, and $Y^3$ is a nitrogen atom or CH.

(3)

The compound or pharmaceutically acceptable salt thereof according to (1) above, wherein in formula (I), $Y^1$ and $Y^2$ are each CH, and $Y^3$ is a nitrogen atom.

(4)

The compound or pharmaceutically acceptable salt thereof according to (1) above, wherein in formula (I), X is an oxygen atom.

(5)

The compound or pharmaceutically acceptable salt thereof according to (1) above, wherein in formula (I), $R^1$ is a hydrogen atom or a $C_1$-$C_6$ alkyl group.

(6)

The compound or pharmaceutically acceptable salt thereof according to (1) above, wherein in formula (I), $R^1$ is a hydrogen atom, a methyl group or an ethyl group.

(7)

The compound or pharmaceutically acceptable salt thereof according to (1) above, wherein in formula (I), $R^2$ is a hydrogen atom or a $C_1$-$C_6$ alkyl group.

(8)

The compound or pharmaceutically acceptable salt thereof according to (1) above, wherein in formula (I), $R^2$ is a methyl group or an ethyl group.

(9)

The compound or pharmaceutically acceptable salt thereof according to (1) above, wherein in formula (I), $R^4$ is a hydrogen atom.

(10)

The compound or pharmaceutically acceptable salt thereof according to (1) above, wherein in formula (I), $R^3$ is a phenyl group, a naphthyl group or an isoquinolinyl group, each of which may be substituted with 1 to 3 substituents selected from the group D [wherein the group D consists of a halogen atom, a $C_1$-$C_6$ alkyl group, a $C_1$-$C_6$ alkoxy group, an amino group which may be substituted with one or two $C_1$-$C_6$ alkyl groups, a morpholino group, and a piperazino group which may be substituted with a $C_1$-$C_6$ alkyl group(s)].

(11)

The compound or pharmaceutically acceptable salt thereof according to (1) above, wherein in formula (I), $R^3$ is a phenyl group whose meta position is substituted with one substituent selected from the group E [wherein the group E consists of an amino group which may be substituted with one or two $C_1$-$C_6$ alkyl groups, a morpholino group, and a piperazino group which may be substituted with a $C_1$-$C_6$ alkyl group(s)].

(12)

The compound or pharmaceutically acceptable salt thereof according to (1) above, wherein in formula (I), $R^5$ is a phenyl group, a thienyl group, a naphthyl group, a dihydrobenzofuranyl group, a benzodioxolyl group, a benzothiadiazolyl group, a benzothienyl group or a quinolinyl group, each of which may be substituted with 1 to 3 substituents selected from the group F [wherein the group F consists of a $C_1$-$C_6$ alkyl group, a halogen atom, a trifluoromethyl group, a $C_1$-$C_6$ alkoxy group, a nitro group, a cyano group, and a $C_2$-$C_7$ alkanoyl group], or a $C_2$-$C_8$ alkenyl group which may be substituted with a phenyl group(s).

(13)

The compound or pharmaceutically acceptable salt thereof according to (1) above, wherein in formula (I), $R^5$ is a phenyl group substituted with two or three halogen atoms or a naphthyl group substituted with one or two halogen atoms.

(14)

A pharmaceutical preparation comprising the compound or pharmaceutically acceptable salt thereof according to any one of (1) to (13) above.

(15)

The pharmaceutical preparation according to (14) above, which is a therapeutic agent for an autoimmune disease such as Crohn's disease, irritable bowel syndrome, Sjogren's syndrome, multiple sclerosis or systemic lupus erythematosus, rheumatoid arthritis, asthma, atopic dermatitis, rejection after organ transplantation, cancer, retinopathy, psoriasis, osteoarthritis, or age-related macular degeneration.

ADVANTAGES OF THE INVENTION

The compounds of the present invention were found to be strong Edg-1($S1P_1$) ligands, as is apparent from the test example described later.

BEST MODE FOR CARRYING OUT THE INVENTION

The present invention will be illustrated in detail below. As used herein, the phrase "excluding the case where $Y^1$ is $CR^A$, $Y^2$ is $CR^B$ and $Y^3$ is $CR^C$" is intended to mean that the aromatic ring containing $Y^1$, $Y^2$ and $Y^3$ as its constituent atoms is not a benzene ring. Namely, it means that at least one of $Y^1$, $Y^2$ and $Y^3$ is a nitrogen atom.

The term "halogen atom" refers to a fluorine atom, a chlorine atom, a bromine atom or an iodine atom.

The term "$C_1$-$C_6$ alkyl group" refers to a linear or branched alkyl group containing 1 to 6 carbon atoms. Examples include a methyl group, an ethyl group, a n-propyl group, an isopropyl group, a n-butyl group, an isobutyl group, a tert-butyl group, a sec-butyl group, a n-pentyl group, an isopentyl group, a neopentyl group, a tert-pentyl group, and a n-hexyl group.

The term "$C_3$-$C_8$ cycloalkyl group" refers to a cycloalkyl group containing 3 to 8 carbon atoms. Examples include a cyclopropyl group, a cyclobutyl group, a cyclopentyl group, and a cyclohexyl group.

The term "$C_2$-$C_8$ alkenyl group" refers to a linear or branched alkenyl group containing 2 to 8 carbon atoms. Examples include a vinyl group, an allyl group, a 1-propenyl group, an isopropenyl group, a 1-butenyl group, a 2-butenyl group, a 3-butenyl group, a 1,3-butadienyl group, a 2-methylallyl group, a 2-methyl-propenyl group, a 2-pentenyl group, and a 3-methyl-but-2-enyl group.

The term "$C_1$-$C_6$ alkoxy group" refers to a linear or branched alkoxy group containing 1 to 6 carbon atoms. Examples include a methoxy group, an ethoxy group, a propoxy group, an isopropoxy group, a butoxy group, an isobutoxy group, a sec-butoxy group, a tert-butoxy group, a pentyloxy group, and a hexyloxy group.

The term "$C_1$-$C_6$ alkylsulfonyl group" refers to a linear or branched alkylsulfonyl group containing 1 to 6 carbon atoms. Examples include a methanesulfonyl group, an ethanesulfonyl group, a propane-2-sulfonyl group, and a hexanesulfonyl group.

The term "$C_1$-$C_6$ alkylsulfonylamino group" refers to a group composed of a $C_1$-$C_6$ alkylsulfonyl group as defined above and an amino group attached thereto. Examples include a methanesulfonylamino group, an ethanesulfonylamino group, a propane-2-sulfonylamino group, and a hexanesulfonylamino group.

The term "$C_2$-$C_7$ alkanoyl group" refers to a linear or branched alkanoyl group containing 2 to 7 carbon atoms. Examples include an acetyl group, a propanoyl group, a butanoyl group, and a hexanoyl group.

The term "$C_1$-$C_6$ alkanoyl group" refers to a linear or branched alkanoyl group containing 1 to 6 carbon atoms. Examples include a formyl group, an acetyl group, a propanoyl group, and a butanoyl group.

The term "$C_1$-$C_6$ alkanoylamino group" refers to a group composed of a $C_1$-$C_6$ alkanoyl group as defined above and an amino group attached thereto. Examples include a formylamino group, an acetylamino group, a propanoylamino group, and a butanoylamino group.

The phrase "amino group which may be substituted with one or two $C_1$-$C_6$ alkyl groups" is intended to include, for example, an amino group, a methylamino group, an ethylamino group, an isopropylamino group, a hexylamino group, a dimethylamino group, a diethylamino group, a diisopropylamino group, and a dihexylamino group.

The phrase "piperazino group which may be substituted with a $C_1$-$C_6$ alkyl group(s)" refers to a piperazino group which may be substituted with a linear or branched alkyl group(s) containing 1 to 6 carbon atoms. Examples include a piperazino group, a methylpiperazino group, and an isopropylpiperazino group.

The term "pharmaceutically acceptable salt" refers to a salt with an alkali metal, an alkaline earth metal, ammonium or an alkylammonium, or a salt with a mineral acid or an organic acid. Examples include a sodium salt, a potassium salt, a calcium salt, an ammonium salt, an aluminum salt, a triethylammonium salt, an acetate salt, a propionate salt, a butyrate salt, a formate salt, a trifluoroacetate salt, a maleate salt, a tartrate salt, a citrate salt, a stearate salt, a succinate salt, an ethylsuccinate salt, a lactobionate salt, a gluconate salt, a glucoheptate salt, a benzoate salt, a methanesulfonate salt, an ethanesulfonate salt, a 2-hydroxyethanesulfonate salt, a benzenesulfonate salt, a paratoluenesulfonate salt, a lauryl sulfate salt, a malate salt, an aspartate salt, a glutamate salt, an adipate salt, a salt with cysteine, a salt with N-acetylcysteine, a hydrochloride salt, a hydrobromide salt, a phosphate salt, a sulfate salt, a hydroiodide salt, a nicotinate salt, an oxalate salt, a picrate salt, a thiocyanate salt, an undecanoate salt, a salt with an acrylate polymer, and a salt with a carboxyvinyl polymer.

The compounds of the present invention may have stereoisomers including optical isomers, diastereoisomers and geometrical isomers. All of these stereoisomers and mixtures thereof also fall within the scope of the present invention. Some of the compounds and intermediates of the present invention may also exist, e.g., as keto-enol tautomers.

Preferred embodiments of the compound of the present invention will be given below.

$Y^1$ is preferably a nitrogen atom or CH, $Y^2$ is preferably $CR^B$, and $Y^3$ is preferably a nitrogen atom or CH. More preferably, $Y^1$ and $Y^2$ are each CH, and $Y^3$ is a nitrogen atom.

A preferred example of X is an oxygen atom.

A preferred example of $R^1$ is a hydrogen atom or a $C_1$-$C_6$ alkyl group. More preferred is a hydrogen atom, a methyl group or an ethyl group, and even more preferred is a methyl group.

A preferred example of $R^2$ is a hydrogen atom or a $C_1$-$C_6$ alkyl group. More preferred is a methyl group or an ethyl group, and even more preferred is an ethyl group.

A preferred example of $R^4$ is a hydrogen atom.

A preferred example of $R^3$ is a phenyl group whose meta position is substituted with one substituent selected from the group E [wherein the group E consists of an amino group which may be substituted with one or two $C_1$-$C_6$ alkyl groups, a morpholino group, and a piperazino group which may be substituted with a $C_1$-$C_6$ alkyl group(s)]. More preferred is a 3-(4-methylpiperazino)phenyl group or a 3-morpholinophenyl group.

A preferred example of $R^5$ is a phenyl group substituted with two or three halogen atoms, or a naphthyl group substituted with one or two halogen atoms. More preferred is a 3,4-dichlorophenyl group, a 2,3,4-trichlorophenyl group or a 5-chloro-2-naphthyl group.

Preferred optically active forms of the compounds of the present invention are those having the following structure.

[Formula 2]

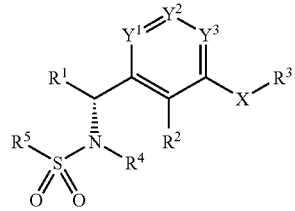

The compounds of the present invention can be synthesized by the procedures shown below, by way of example. It should be noted that the following procedures are shown for illustrative purposes, and synthesis procedures for the compounds of the present invention are not limited thereto.

(Scheme 1)
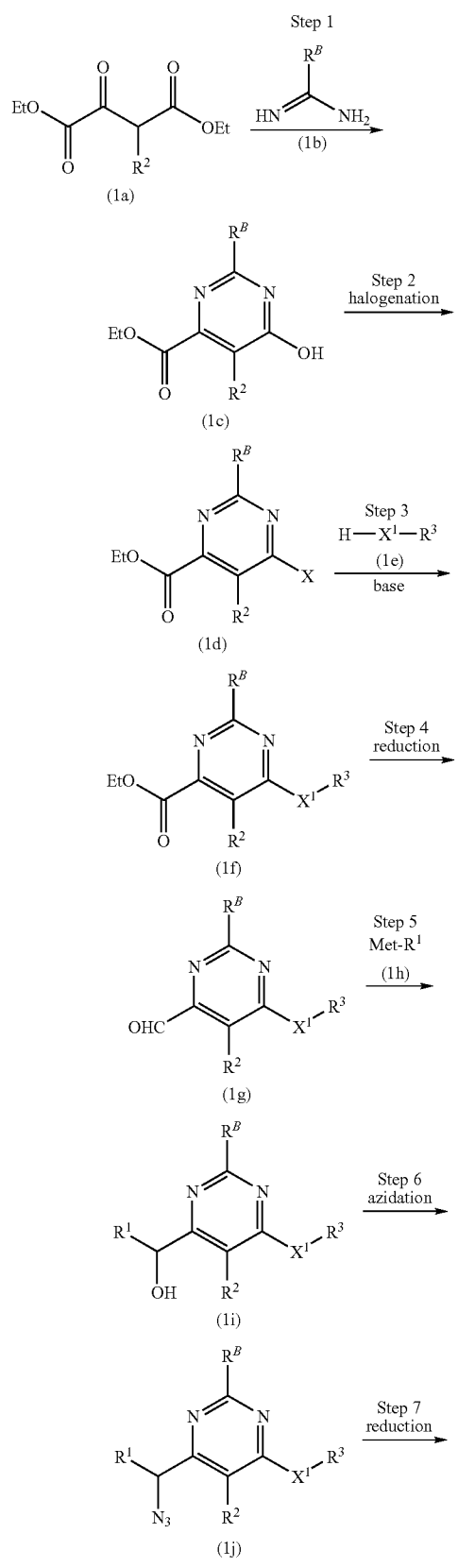
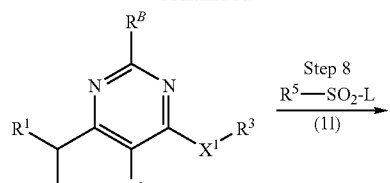
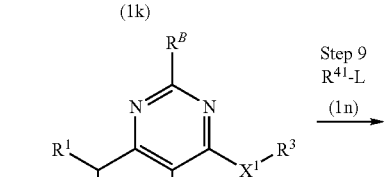
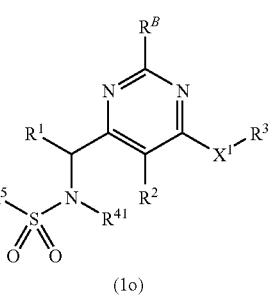
(Scheme 2)
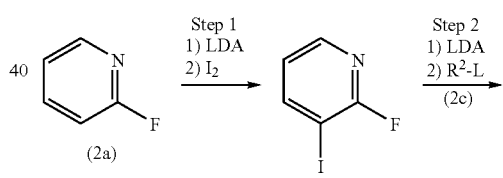
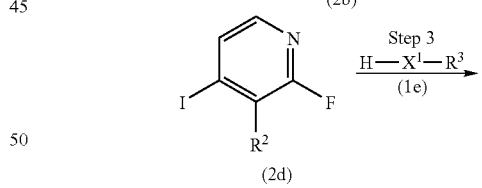
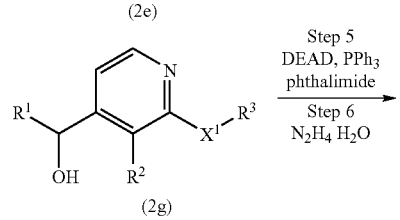

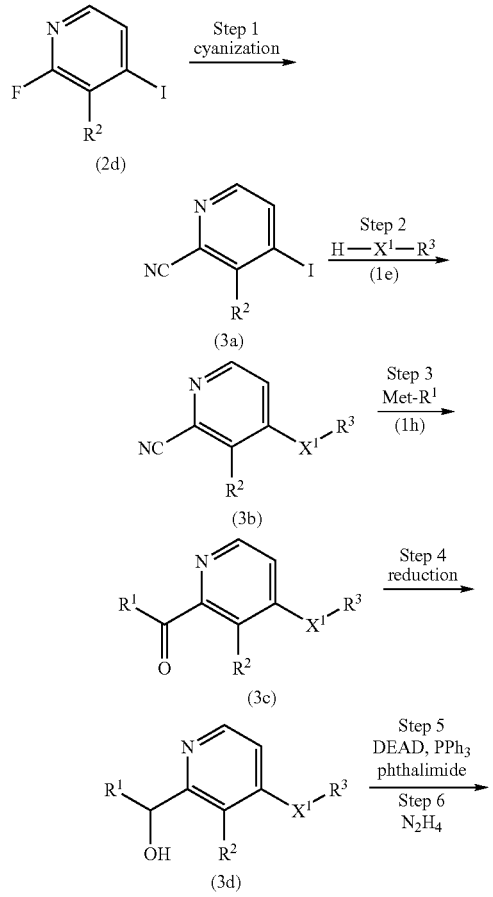

(Scheme 3)

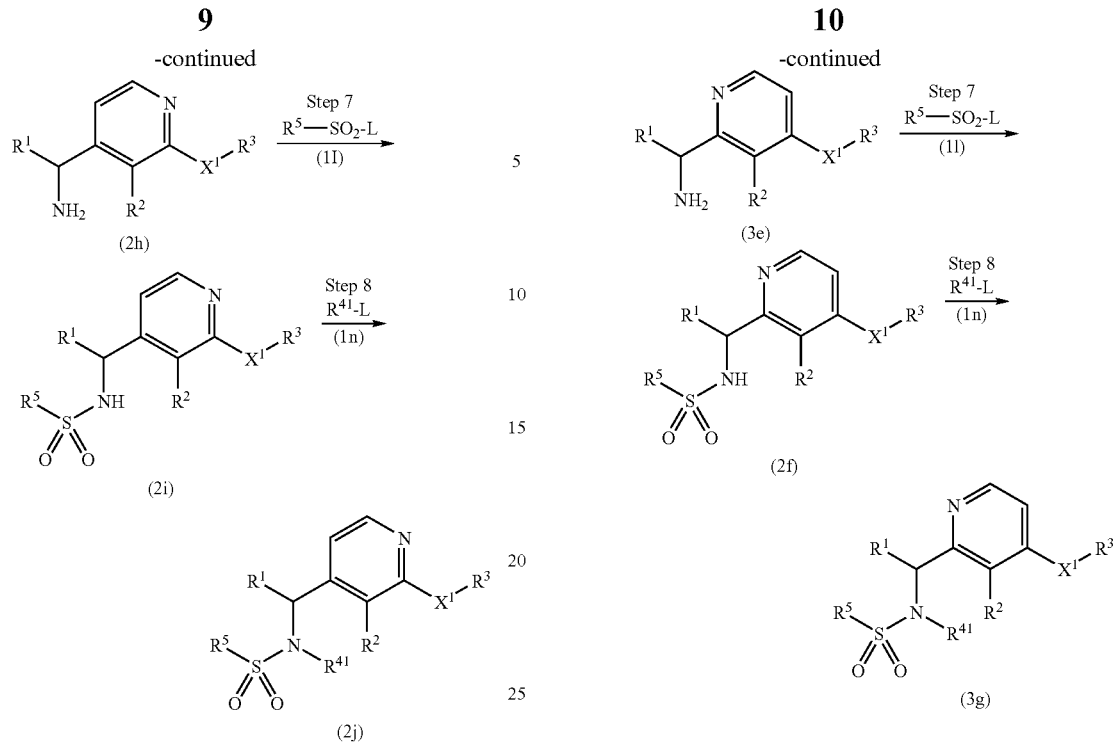

(Scheme 4)

In the above steps, $Y^1$, $Y^2$, $Y^3$, $R^B$, $R^1$, $R^2$, $R^3$, $R^4$, $R^5$ and X are as defined above, $R^{41}$ is the same as defined for $R^4$ excluding a hydrogen atom, $X^1$ represents an oxygen atom, a sulfur atom or a group represented by the formula —$NR^6$— (wherein $R^6$ represents a hydrogen atom or a $C_1$-$C_6$ alkyl group), Met represents a typical metal or a complex between the typical metal and its ligand such as a halogen atom etc. (e.g., Li, Na, MgCl, MgBr), and L represents a leaving group (wherein the leaving group may be, for example, a halogen atom such as a chlorine atom, a bromine atom or an iodine atom, an acetyloxy group, a methanesulfonyloxy group, or a p-toluenesulfonyloxy group).

Scheme 1

Step 1: A compound represented by formula (1a) may be reacted with a compound represented by formula (1b) to obtain a compound represented by formula (1c).

Step 2: The compound represented by formula (1c) may be reacted with a halogenating agent to obtain a compound represented by formula (1d). Examples of a halogenating agent include $POCl_3$, $PCl_5$, and $SOCl_2$. The amount of the halogenating agent to be used is generally 1 to 10 equivalents, preferably 5 to 10 equivalents of the compound represented by formula (1c). When a solvent is required, any solvent may be used as long as it is inert to the reaction, including halogenated solvents (e.g., $CCl_4$, $CHCl_3$, $CH_2Cl_2$), DMF, DMA, NMP, DMPU, HMPA, DMSO, or mixed solvents thereof. The reaction temperature ranges from 0° C. to the solvent reflux temperature, preferably room temperature to the solvent reflux temperature. Although the reaction time will vary depending on the reaction temperature and/or starting compound, it is generally 1 hour to 12 hours.

Step 3: The compound represented by formula (1d) may be reacted with a compound represented by formula (1e) in the presence of a base with or without a solvent to obtain a compound represented by formula (1f). The amount of compound (1e) to be used is generally 1 to 5 equivalents, preferably 1 to 3 equivalents of the compound represented by formula (1d). Examples of a base include alkali metal salts (e.g., $Na_2CO_3$, $K_2CO_3$, $Cs_2CO_3$, $NaHCO_3$, $KHCO_3$, NaOH, NaH, $NaNH_2$, t-BuOK, t-BuONa), amines (e.g., $Et_3N$, $iPr_2NEt$, $iPr_2NH$, pyrrolidine, piperidine), AcONa, and AcOK. The amount of the base to be used is generally 1 to 10 equivalents, preferably 1 to 3 equivalents of the compound represented by formula (1d). The reaction temperature ranges from 0° C. to 300° C., and the reaction may be accomplished, e.g., under normal pressure, under elevated pressure or under microwave irradiation. Examples of a reaction solvent available for use include ethers (e.g., dioxane, THF, $Et_2O$), DMF, DMA, NMP, DMPU, HMPA, DMSO, or mixed solvents thereof. If necessary, an additive is added. Examples of an additive include metal salts (e.g., CuI, CuCl), or copper powder. Although the reaction time will vary depending on the reaction temperature and/or starting compound, it is generally 1 hour to 12 hours.

Step 4: The compound represented by formula (1f) may be reacted with a reducing agent to obtain a compound represented by formula (1g). Examples of a reducing agent include $NaBH_4$, $KBH_4$, $LiB(H)Et_3$, $LiB(sec-Bu)_3H$, $(i-Bu)_2AlH$, $AlH(O-t-Bu)_3$, $LiAlH_4$, $LiHAl(O-t-Bu)_3$, and $NaH_2Al(OCH_2CH_2OCH_3)$. The amount of the reducing agent is 0.5 to 5 equivalents, preferably 0.5 to 1.2 equivalents of the compound represented by formula (1f). Examples of a solvent available for use include ethers (e.g., dioxane, THF, diethyl ether), hexane, benzene, toluene, or mixed solvents thereof. The reaction temperature ranges from −78° C. to room temperature, preferably −78° C. to 0° C. Although the reaction time will vary depending on the reaction temperature and/or starting compound, it is generally 30 minutes to 4 hours.

Step 5: The compound represented by formula (1g) may be reacted with a compound represented by formula (1h) to obtain a compound represented by formula (1i). The amount of the compound represented by formula (1h) to be used is 1 to 10 equivalents, preferably 1.1 to 1.5 equivalents of the compound represented by formula (1g). Examples of a solvent available for use include ethers (e.g., dioxane, THF, $Et_2O$) or mixed solvents thereof. The reaction temperature ranges from −78° C. to room temperature, preferably −30° C. to 0° C. Although the reaction time will vary depending on the reaction temperature and/or starting compound, it is generally 30 minutes to 24 hours.

Step 6: The compound represented by formula (1i) may be reacted with methanesulfonyl chloride, p-toluenesulfonyl chloride, triflate anhydride or the like in a solvent and, if necessary, in the presence of a base such as pyridine or triethylamine, followed by reaction with an azidating agent (e.g., $NaN_3$, $LiN_3$, $Zn(N_3)_2$), or alternatively, may be directly treated with diethyl azodicarboxylate (DEAD)/$PPh_3$/$NH_3$, diphenylphosphorylazide (DPPA)/1,8-diazabicyclo[5.4.0]undec-7-ene (DBU), $Zn(N_3)_2$/2 pyridine or the like to obtain a compound represented by formula (1j). Examples of a solvent include ethers (e.g., dioxane, THF), halogenated solvents (e.g., $CH_3CN$, $CCl_4$, $CHCl_3$, $CH_2Cl_2$), benzene, and toluene.

Step 7: The compound represented by formula (1j) may be reacted with a reducing agent in a solvent and, if necessary, in the presence of a catalyst (e.g., Pd/C, $Pd(OH)_2$/C, $PtO_2$) to obtain a compound represented by formula (1k). Examples of a reducing agent include hydrogen, ammonium formate, hydrazine, $PPh_3$, and Mg. Examples of a solvent include ethers (e.g., dioxane, THF, $Et_2O$), alcohols (e.g., MeOH, EtOH), and AcOEt.

Step 8: The compound represented by formula (1k) may be reacted with a compound represented by formula (1l) in the presence of a base with or without a solvent, followed by salt formation as needed to obtain a compound represented by formula (1m) or a pharmaceutically acceptable salt thereof. The amount of the compound represented by formula (1l) to be used is generally 1 to 5 equivalents, preferably 1 to 1.2 equivalents of the compound represented by formula (1k). Examples of a base available for use include alkali metal hydroxides (e.g., NaOH, KOH), alkali metal salts (e.g., $NaHCO_3$, $K_2CO_3$), and amines (e.g., $Et_3N$, $iPr_2NEt$, $iPr_2NH$). The amount of the base is generally 1 to 10 equivalents, preferably 1.0 to 3.0 equivalents of the compound represented by formula (1k). The reaction temperature ranges from 0° C. to the solvent reflux temperature, preferably 0° C. to room temperature. When a solvent is required, any solvent may be used as long as it is inert to the reaction, including halogenated hydrocarbons (e.g., $CHCl_3$, $CH_2Cl_2$), ethers (e.g., dioxane, THF, $Et_2O$), or mixed solvents thereof. Although the reaction time will vary depending on the reaction temperature and/or starting compound, it is generally 30 minutes to 24 hours.

Step 9: The compound represented by formula (1m) may be reacted with a compound represented by formula (1n) in the presence of a base with or without a solvent, followed by salt formation as needed to obtain a compound represented by formula (1o) or a pharmaceutically acceptable salt thereof. The amount of the compound represented by formula (1n) to be used is 1 to 10 equivalents, preferably 1.1 to 1.5 equivalents of the compound represented by formula (1m). Examples of a base available for use include alkali metal hydroxides (e.g., NaOH, KOH), alkali metal salts (e.g., $NaHCO_3$, $K_2CO_3$), and amines (e.g., $Et_3N$, $iPr_2NEt$, $iPr_2NH$). The amount of the base is generally 1 to 10 equivalents, preferably 1.0 to 3.0 equivalents of the compound represented by formula (1m). The reaction temperature ranges from 0° C. to the solvent reflux temperature, preferably 0° C. to room temperature. When a solvent is required, any solvent may be used as long as it is inert to the reaction, including water, ethers (e.g., dioxane, THF, $Et_2O$), DMF, DMA, NMP, DMPU, HMPA, DMSO, or mixed solvents thereof. Although the reaction time will vary depending on the reaction temperature and/or starting compound, it is generally 30 minutes to 24 hours.

Scheme 2

Steps 1 and 2: 2-Fluoropyridine may be reacted with LDA and then with iodine, and the resulting 2-fluoro-3-iodo-pyridine may be reacted with LDA and then with a compound represented by formula (2c) to obtain a compound represented by formula (2d) (J. Org. Chem., 1993, 58, 7832-7838).

Step 3: Starting from the compound represented by formula (2d) and the compound represented by formula (1e), the same procedure as shown in Step 3 of Scheme 1 may be repeated to obtain a compound represented by formula (2e).

Step 4: The compound represented by formula (2e) may be reacted with a base and then with a compound represented by formula (2f) to obtain a compound represented by formula (2g). Examples of a base include iPrMgCl, n-BuLi, and LDA. The amount of the base to be used is 1 to 10 equivalents, preferably 1.1 to 1.5 equivalents of the compound represented by formula (2e). The amount of the compound represented by formula (20 to be used is 1 to 10 equivalents, preferably 2 to 3 equivalents of the compound represented by formula (2e). Examples of a solvent available for use include ethers (e.g., dioxane, THF, $Et_2O$) or mixed solvents thereof. The reaction temperature ranges from $-78°$ C. to room temperature, preferably $-78°$ C. to $-30°$ C. Although the reaction time will vary depending on the reaction temperature and/or starting compound, it is generally 30 minutes to 24 hours.

Steps 5 and 6: The compound represented by formula (2g) may be reacted with phthalimide in the presence of DEAD and $PPh_3$, and the resulting compound may be reacted with hydrazine to obtain a compound represented by formula (2h). Alternatively, the same procedure as shown in Steps 6 and 7 of Scheme 1 may also be used to obtain the compound represented by formula (2h) from the compound represented by formula (2g).

Step 7: Starting from the compound represented by formula (2h) and the compound represented by formula (1l), the same procedure as shown in Step 8 of Scheme 1 may be repeated to obtain a compound represented by formula (2l).

Step 8: Starting from the compound represented by formula (2l) and the compound represented by formula (1n), the same procedure as shown in Step 9 of Scheme 1 may be repeated to obtain a compound represented by formula (2j).

Scheme 3

Step 1: The compound represented by formula (2d) obtained in Steps 1 and 2 of Scheme 3 may be cyanized to obtain a compound represented by formula (3a). Examples of a cyanizing agent include NaCN, KCN, and CuCN. Examples of a solvent available for use include DMF, DMA, NMP, DMPU, HMPA, DMSO, or mixed solvents thereof. If necessary, an additive is added. Examples of an additive include crown ethers (e.g., 15-crown-5 ether, 18-crown-6 ether), and phase-transfer catalysts (e.g., $nBu_4NOH$).

Step 2: Starting from the compound represented by formula (3a) and the compound represented by formula (1e), the same procedure as shown in Step 3 of Scheme 1 may be repeated to obtain a compound represented by formula (3b).

Step 3: Starting from the compound represented by formula (3b) and the compound represented by formula (1h), a compound represented by formula (3c) may be obtained. The amount of the compound represented by formula (1h) to be used is 1 to 10 equivalents, preferably 3 to 5 equivalents of the compound represented by formula (3b). Examples of a solvent available for use include ethers (e.g., dioxane, THF, $Et_2O$) or mixed solvents thereof. The reaction temperature ranges from $-78°$ C. to the solvent reflux temperature, preferably $0°$ C. to room temperature. Although the reaction time will vary depending on the reaction temperature and/or starting compound, it is generally 30 minutes to 24 hours.

Step 4: The compound represented by formula (3c) may be reacted with a reducing agent in a solvent to obtain a compound represented by formula (3d). Examples of a reducing agent include $NaBH_4$, $KBE_4$, LiB(sec-Bu)$_3$H, (i-Bu)$_2$AlH, and $LiAlH_4$. The amount of the reducing agent is 0.5 to 5 equivalents, preferably 0.5 to 1.2 equivalents of the compound represented by formula (3c). Examples of a solvent include ethers (e.g., dioxane, THF, $Et_2O$), and alcohols (e.g., MeOH, EtOH). The reaction temperature ranges from $-78°$ C. to the solvent reflux temperature, preferably $0°$ C. to room temperature. Although the reaction time will vary depending on the reaction temperature and/or starting compound, it is generally 30 minutes to 2 hours.

Steps 5 and 6: Starting from the compound represented by formula (3d), the same procedure as shown in Steps 5 and 6 of Scheme 2 may be repeated to obtain a compound represented by formula (3e).

Step 7: Starting from the compound represented by formula (3e) and the compound represented by formula (1l), the same procedure as shown in Step 8 of Scheme 1 may be repeated to obtain a compound represented by formula (3f).

Step 8: Starting from the compound represented by formula (3f) and the compound represented by formula (1n), the same procedure as shown in Step 9 of Scheme 1 may be repeated to obtain a compound represented by formula (3g).

Scheme 4

A compound obtained as shown in Schemes 1 to 3, in which $X^1$ is a sulfur atom, i.e., a compound represented by formula (4a) may be reacted with an oxidizing agent, followed by salt formation as needed to obtain compounds represented by formulae (4b) and (4c) or pharmaceutically acceptable salts thereof. Examples of an oxidizing agent available for use include organic peracids (e.g., m-chloroperbenzoic acid, magnesium monoperphthalate hexahydrate, peracetic acid, performic acid), inorganic and organic peroxides (e.g., hydrogen peroxide, urea hydrogen peroxide adduct/phthalic anhydride, tert-butyl hydroperoxide, cumene hydroperoxide), sodium periodate, Oxone®, N-bromosuccinimide, N-chlorosuccinimide, chloramine-T, tert-butyl hypochlorite, iodobenzene diacetate, and bromine-1,4-diazabicyclo[2,2,2]octane addition complex. The amount of the oxidizing agent to be used is 1 to 10 equivalents, preferably 1 to 3 equivalents of the compound represented by formula (4a). When a solvent is required, any solvent may be used as long as it is inert to the reaction, including halogenated hydrocarbons such as methylene chloride and chloroform. The reaction temperature ranges from $-78°$ C. to the solvent reflux temperature, preferably $0°$ C. to $40°$ C. Although the reaction time will vary depending on the reaction temperature and/or starting compound, it is generally 30 minutes to 24 hours.

In the synthesis routes shown in the above schemes, the sequence of the steps may also be altered as appropriate to synthesize the compounds of the present invention.

For use as pharmaceutical preparations, the compounds of the present invention may be supplemented with commonly used excipients, extenders, pH adjustors, solubilizers and so on, and then formulated using standard techniques into tablets, granules, pills, capsules, powders, solutions, suspensions, injections, etc. The pharmaceutical preparations thus obtained can be administered as oral or parenteral formulations.

The compounds of the present invention may be given to adult patients at 1 to 1000 mg per day as a single dose or in divided doses. This dosage may be increased or decreased as appropriate for the type of disease, the age, body weight and symptom of a patient, etc.

The present invention will be further described in more detail by way of the following examples and test example.

EXAMPLE 1

3,4-Dichloro-N-[1-(5-ethyl-2-methyl-6-p-toluoyloxy-pyrimidin-4-yl)-ethyl]-benzenesulfonamide (Compound 1)

[Formula 7]

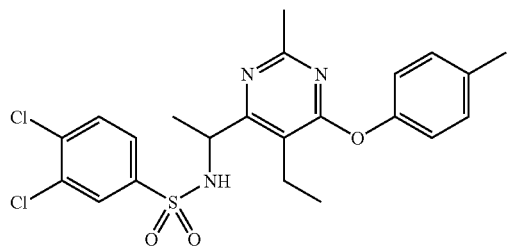

5-Ethyl-6-hydroxy-2-methyl-pyrimidine-4-carboxylic acid ethyl ester

[Formula 8]

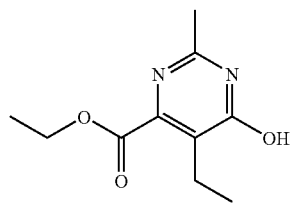

(1) Under a nitrogen atmosphere, a NaOEt solution prepared from Na (1.63 g) and EtOH (30 ml) was added dropwise to acetamidine hydrochloride (6.69 g) in EtOH (50 ml). Insoluble materials were filtered off, and the filtrate was added to 2-ethyl-3-oxo-succinic acid diethyl ester (15.3 g). The reaction mixture was heated under reflux for 21 hours and then evaporated to remove the solvent, and the resulting residue was purified by column chromatography (OH-type SiO$_2$, AcOEt/hexane=0% to 25%) to give the titled compound (3.71 g, orange solid).

$^1$H NMR (600 MHz, DMSO-D6) δ ppm: 1.02 (t, J=7.3 Hz, 3 H), 1.28 (t, J=7.2 Hz, 3 H), 2.26 (s, 3 H), 2.39 (q, J=7.3 Hz, 2 H), 4.29 (q, J=7.2 Hz, 2 H)

6-Chloro-5-ethyl-2-methyl-pyrimidine-4-carboxylic acid ethyl ester

[Formula 9]

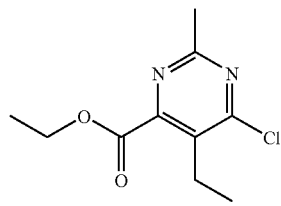

(2) Under a nitrogen atmosphere, to a solution of the compound obtained in Example 1-(1) (1.42 g) in 1,2-dichloroethane (3 ml), POCl$_3$ (3.2 ml) was added and heated under reflux for 1.5 hours. The reaction mixture was cooled to 0° C., neutralized with NaOH (2.0 M in water) and extracted with CHCl$_3$. The organic layer was dried over MgSO$_4$, filtered and then evaporated under reduced pressure to remove the solvent. The resulting crude product was purified by column chromatography (OH-type SiO$_2$, AcOEt/hexane=0% to 25%) to give the titled compound (1.11 g, colorless oil).

$^1$H NMR (600 MHz, DMSO-D6) δ ppm: 1.16 (t, J=7.5 Hz 3 H), 1.33 (t, J=7.2 Hz, 3 H), 2.61 (s, 3 H), 2.72 (q, J=7.5 Hz, 2 H), 4.41 (q, J=7.2 Hz, 2 H)

5-Ethyl-2-methyl-6-p-toluoyloxy-pyrimidine-4-carboxylic acid ethyl ester

[Formula 10]

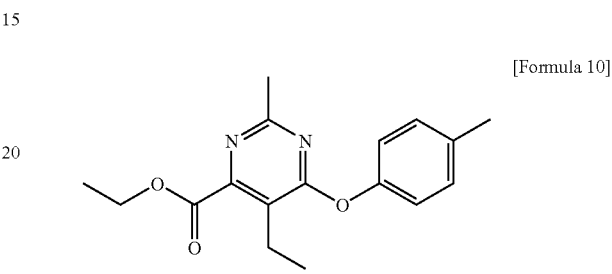

(3) To a solution of 4-cresol (1.02 ml) in DMF (20 ml), NaH (388 mg, 60% in mineral oil) was added at room temperature and stirred at room temperature for 10 minutes, followed by addition of the compound obtained in Example 1-(2) (1.11 g) and stirring at room temperature for an additional 10 minutes. The reaction mixture was diluted with saturated aqueous ammonium chloride and extracted with AcOEt. The organic layer was washed with brine, dried over Na$_2$SO$_4$, filtered and then evaporated under reduced pressure to remove the solvent. The resulting crude product was purified by column chromatography (NH-type SiO$_2$, AcOEt/hexane=0% to 25%) to give the titled compound (1.06 g, colorless oil).

$^1$H NMR (600 MHz, CDCl$_3$) δ ppm: 1.28 (t, J=7.5 Hz, 3 H), 1.44 (t, J=7.2 Hz, 3 H), 2.38 (s, 3 H), 2.51 (s, 3 H), 2.83 (q, J=7.5 Hz, 2 H), 4.47 (q, J=7.2 Hz, 2 H), 6.99-7.04 (m, 2 H), 7.19-7.24 (m, 2 H)

5-Ethyl-2-methyl-6-p-toluoyloxy-pyrimidine-4-carbaldehyde

[Formula 11]

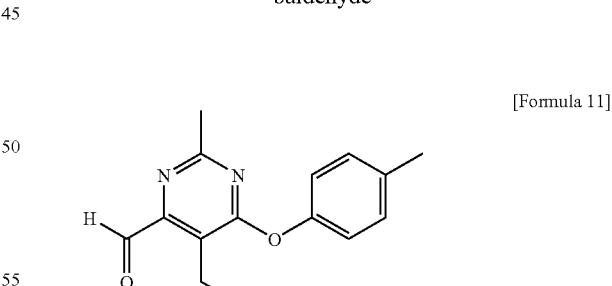

(4) Under a nitrogen atmosphere, to a solution of the compound obtained in Example 1-(3) (552 mg) in toluene (10 ml), DiBAL-H (2.76 ml, 1.0 M in toluene) was added at −78° C. and stirred at the same temperature for 2.5 hours, followed by addition of DiBAL-H (2.76 ml, 1.0 M in toluene) and stirring at the same temperature for an additional 1.0 hour. The reaction mixture was diluted with HCl (2.0 M in water) and extracted with CHCl$_3$. The organic layer was dried over MgSO$_4$, filtered and then evaporated under reduced pressure to remove the solvent. The resulting crude product was purified by column chromatography (OH-type SiO$_2$, AcOEt/hexane=0% to 25%) to give the titled compound (443 mg, colorless solid).

$^1$H NMR (600 MHz, CDCl$_3$) δ ppm: 1.26 (t, J=7.5 Hz, 3 H), 2.39 (s, 3 H), 2.55 (s, 3 H), 3.11 (q, J=7.5 Hz, 2 H), 7.01-7.05 (m, 2 H), 7.21-7.25 (m, 2 H), 10.10 (s, 1 H)

1-(5-Ethyl-2-methyl-6-p-toluoyloxy-pyrimidin-4-yl)-ethanol

[Formula 12]

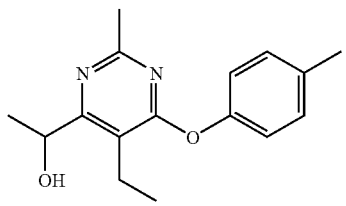

(5) To a solution of the compound obtained in Example 1-(4) (443 mg) in Et$_2$O (10 ml), MeMgBr (0.75 ml, 3.0 mmol, in Et$_2$O) was added at −30° C. under a nitrogen atmosphere. After stirring at 0° C. for 1 hour, the reaction mixture was diluted with saturated aqueous ammonium chloride and extracted with AcOEt. The organic layer was dried over Na$_2$SO$_4$, filtered and then evaporated under reduced pressure to remove the solvent. The resulting crude product was purified by column chromatography (OH-type SiO$_2$, AcOEt/hexane=0% to 25%) to give the titled compound (422 mg, colorless solid).

$^1$H NMR (600 MHz, CDCl$_3$) δ ppm: 1.24 (t, J=7.3 Hz, 3 H), 1.43 (d, J=6.4 Hz, 3 H), 2.38 (s, 3 H), 2.46 (s, 3 H), 2.58-2.73 (m, 2 H), 4.55-4.62 (m, 1 H), 4.95-5.03 (m, 1 H), 6.99-7.04 (m, 2 H), 7.18-7.22 (m, 2 H)

4-(1-Azidoethyl)-5-ethyl-2-methyl-6-p-toluoyloxy-pyrimidine

[Formula 13]

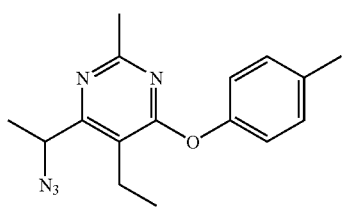

(6) To a solution of the compound obtained in Example 1-(5) (422 mg) in toluene (10 ml), diphenylphosphorylazide (DPPA) (0.50 ml) and 1,8-diazabicyclo[5,4,0]undec-7-ene (DBU) (0.70 ml) were added and stirred at 50° C. for 7.5 hours. To this mixture, DPPA (0.50 ml) and DBU (0.35 ml) were further added and stirred overnight at 60° C. The reaction mixture was diluted with water and extracted with AcOEt. The organic layer was washed with brine, dried over MgSO$_4$, filtered and then evaporated to remove the solvent. The resulting crude product was purified by column chromatography (NH-type silica gel, AcOEt/hexane=0% to 10%) to give the titled compound (370 mg, colorless oil).

$^1$H NMR (600 MHz, CDCl$_3$) δ ppm: 1.23 (m, 3 H), 1.63 (d, J=6.8 Hz, 3 H), 2.38 (s, 3 H), 2.47 (s, 3 H), 2.68-2.81 (m, 2 H), 4.67 (q, J=6.8 Hz, 1 H), 6.99-7.03 (m, 2 H), 7.18-7.22 (m, 2 H)

1-(5-Ethyl-2-methyl-6-p-toluoyloxy-pyrimidin-4-yl)-ethylamine

[Formula 14]

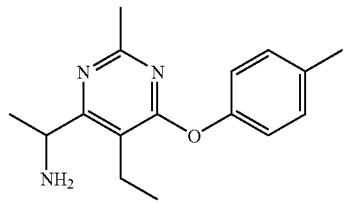

(7) A mixture of the compound obtained in Example 1-(6) (370 mg) and palladium on activated carbon (100 mg, Pd 10 wt. %) in AcOEt (10 ml) was stirred under a hydrogen atmosphere (about 1 atm) at room temperature for 1.5 hours. The reaction mixture was filtered through celite, and the filtrate was concentrated to give the titled compound (330 mg, colorless solid).

$^1$H NMR (600 MHz, CDCl$_3$) δ ppm: 1.22 (t, J=7.6 Hz, 3 H), 1.39 (d, J=6.7 Hz, 3 H), 2.37 (s, 3 H), 2.45 (s, 3 H), 2.65-2.79 (m, 2 H), 4.32 (q, J=6.7 Hz, 1 H), 6.98-7.03 (m, 2 H), 7.16-7.21 (m, 2 H)

3,4-Dichloro-N-[1-(5-ethyl-2-methyl-6-p-toluoyloxy-pyrimidin-4-yl)-ethyl]-benzenesulfonamide (Compound 1)

[Formula 15]

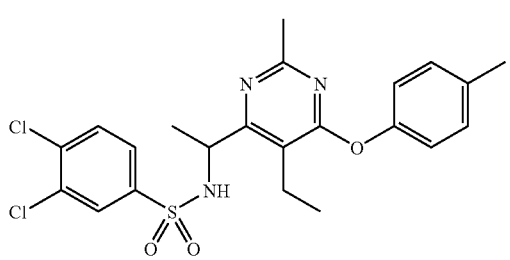

(8) To a solution of the compound obtained in Example 1-(7) (126 mg) in THF (3.0 ml), Et$_3$N (0.20 ml) and 3,4-dichlorobenzenesulfonyl chloride (171 mg) were added at room temperature and stirred at room temperature for 1 hour. The reaction mixture was concentrated, and the resulting crude product was purified by silica gel column chromatography (NH-type SiO$_2$, AcOEt/hexane=50%), followed by recrystallization (AcOEt/Hexane) to give the titled compound (Compound 1) (177 mg, colorless powder).

$^1$H NMR (600 MHz, DMSO-D6) δ ppm: 1.16 (t, J=7.6 Hz, 3 H), 1.33 (d, J=6.9 Hz, 3 H), 2.12 (s, 3 H), 2.33 (s, 3 H), 2.53-2.70 (m, 2 H), 4.72-4.81 (m, 1 H), 6.93-7.00 (m, 2 H), 7.20-7.26 (m, 2 H), 7.48-7.54 (m, 1 H), 7.64-7.69 (m, 1 H), 7.70-7.74 (m, 1 H), 8.55 (br s, 1 H)

EXAMPLE 2

3,4-Dichloro-N-(1-{3-ethyl-2-[3-(4-methyl-piperazin-1-yl)-phenoxy]-pyridin-4-yl}-ethyl)-benzenesulfonamide (Compound 3)

[Formula 16]

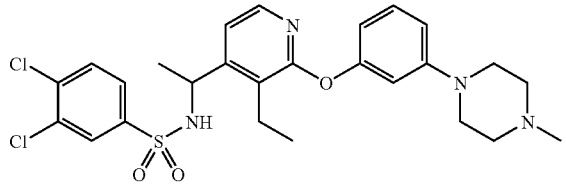

2-Fluoro-3-iodo-pyridine

[Formula 17]

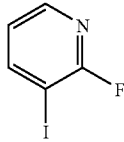

(1) Under a nitrogen atmosphere, to a solution prepared by adding lithium diisopropylamide (54.1 ml, 2 M in heptane/THF/ethylbenzene) to THF (100 ml), a solution of 2-fluoropyridine (10.503 g) in THF (10 ml) was added dropwise at −78° C. and stirred at the same temperature for 4 hours. To the reaction mixture, a solution of iodine (13.728 g) in THF (10 ml) was added dropwise and stirred at the same temperature for 2 hours. After addition of water (5 ml), the reaction mixture was warmed to room temperature, diluted with brine and then extracted with ether. The organic layer was dried over $Na_2SO_4$, filtered and then evaporated under reduced pressure to remove the solvent. The resulting crude product was purified by column chromatography (acidic OH-type $SiO_2$, AcOEt/hexane=9%) to give the titled compound (8.94 g, light-yellow oil).

$^1$H NMR (200 MHz, $CDCl_3$) δ ppm: 6.93-7.00 (m, 1H), 8.13-8.22 (m, 2H)

3-Ethyl-2-fluoro-4-iodo-pyridine

[Formula 18]

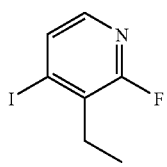

(2) Under a nitrogen atmosphere, to a solution prepared by adding lithium diisopropylamide (15.0 ml, 2 M in heptane/THF/ethylbenzene) to THF (30 ml), a solution of the compound synthesized in Example 2-(1) (6.68 g) in THF (10 ml) was added dropwise at −78° C. and stirred at the same temperature for 1 hour. To the reaction mixture, a solution of ethyl iodide (4.67 g) in THF (10 ml) was added dropwise and stirred at the same temperature for 4 hours. After addition of water (5 ml), the reaction mixture was warmed to room temperature, diluted with brine and then extracted with ether. The organic layer was dried over $Na_2SO_4$, filtered and then evaporated under reduced pressure to remove the solvent. The resulting crude product was purified by column chromatography (acidic OH-type $SiO_2$, AcOEt/hexane=9% to 18%) to give the titled compound (2.554 g, yellow oil).

$^1$H NMR (200 MHz, $CDCl_3$) δ ppm: 1.17 (t, J=7.5 Hz, 3 H), 2.83 (q, J=7.5 Hz, 2 H), 7.59 (d, J=5.3 Hz, 1 H), 7.67 (d, J=5.3 Hz, 1 H)

1-[3-(3-Ethyl-4-iodo-pyridin-2-yloxy)-phenyl]-4-methyl-piperazine

[Formula 19]

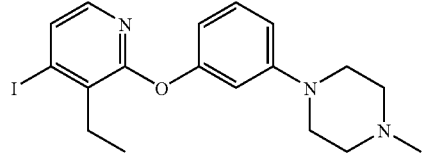

(3) Under a nitrogen atmosphere, to a solution of 3-(4-methyl-piperazin-1-yl)-phenol (505 mg) in DMF (5 ml), sodium hydride (115 mg) was added and stirred at room temperature for 15 minutes. To the reaction mixture, the compound obtained in Example 2-(2) (549 mg) was added and stirred at 130° C. for 1 hour. The reaction mixture was filtered and then concentrated, and the resulting crude product was purified by column chromatography (NH-type $SiO_2$, AcOEt/hexane=50%) to give the titled compound (882 mg, light-yellow solid).

$^1$H NMR (200 MHz, $CDCl_3$) δ ppm: 1.21 (t, J=7.5 Hz, 3 H), 2.34 (s, 3 H), 2.52-2.57 (m, 4 H), 2.87-2.98 (m, 2 H), 3.20-3.25 (m, 4 H), 6.53 (dd, J=7.9, 2.2 Hz, 1 H), 6.64 (t, J=2.2 Hz, 1 H), 6.77 (dd, J=7.9, 2.2 Hz, 1 H), 7.25 (t, J=7.9 Hz, 1 H), 7.39 (d, J=5.3 Hz, 1 H), 7.60 (d, J=5.3 Hz, 1 H)

1-{3-Ethyl-2-[3-(4-methyl-piperazin-1-yl)-phenoxy]-pyridin-4-yl}-ethanol

[Formula 20]

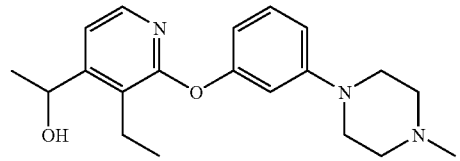

(4) Under a nitrogen atmosphere, to a solution of the compound obtained in Example 2-(3) (665 mg) in THF (2 ml), isopropylmagnesium chloride (2.4 ml, 1 M in THF) was added at −50° C. and stirred at the same temperature for 2 hours. To the reaction mixture, acetaldehyde (208 mg) was added and stirred at room temperature for 2 hours. The reaction mixture was diluted with brine and extracted with THF-ether. After drying over $Na_2SO_4$ and filtration, the solvent was distilled off under reduced pressure. The resulting crude product was purified by column chromatography (NH-type SiO$_2$, MeOH/CHCl$_3$=0% to 5%) to give the titled compound (308 mg, light-yellow oil).

$^1$H NMR (200 MHz, CDCl$_3$) δ ppm: 1.23 (t, J=7.5 Hz, 3 H), 1.49 (d, J=6.6 Hz, 3 H), 2.32 (s, 3 H), 2.52-2.57 (m, 4 H), 2.68-2.82 (m, 2 H), 3.19-3.24 (m, 4 H), 5.18 (q, J=6.6 Hz, 1 H), 6.53 (dd, J=8.0, 2.2 Hz, 1 H), 6.65 (t, J=2.2 Hz, 1 H), 6.72 (dd, J=8.0, 2.2 Hz, 1 H), 7.18 (d, 1 H), 7.24 (t, J=8.0 Hz, 1 H), 8.02 (d, J=5.3 Hz, 1 H)

2-(1-{3-Ethyl-2-[3-(4-methyl-piperazin-1-yl)-phenoxy]-pyridin-4-yl}-ethyl)-isoindole-1,3-dione

[Formula 21]

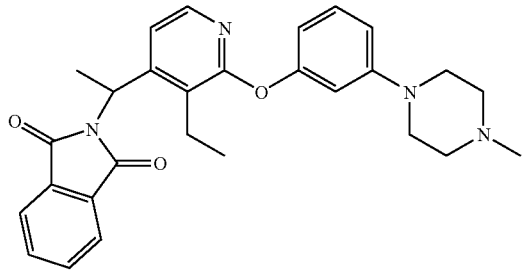

(5) Under a nitrogen atmosphere, to a solution of the compound obtained in Example 2-(4) (201 mg), triphenylphosphine (232 mg) and phthalimide (113 mg) in THF (10 ml), diethyl azodicarboxylate (DEAD, 113 mg, 40% in toluene) was added at 0° C. and stirred at the same temperature for 2 hours. The reaction mixture was concentrated, and the resulting crude product was purified by column chromatography (acidic OH-type SiO$_2$, MeOH/CHCl$_3$=0% to 9%) to give the titled compound (227 mg, light-yellow solid).

$^1$H NMR (200 MHz, CDCl$_3$) δ ppm: 1.19 (t, J=7.5 Hz, 3 H), 1.92 (d, J=7.0 Hz, 3 H), 2.33 (s, 3 H), 2.51-2.56 (m, 4 H), 3.18-3.23 (m, 4 H), 5.77 (q, J=7.0 Hz, 1 H), 6.52 (dd, J=7.9, 2.2 Hz, 1 H), 6.63 (t, J=2.2 Hz, 1 H), 6.72 (dd, J=7.9, 2.2 Hz, 1 H), 7.20 (d, J=8.3 Hz, 1 H), 7.39 (d, J=5.3 Hz, 1 H), 7.70-7.76 (m, 4 H), 7.79-7.86 (m, 4 H), 8.01 (d, J=5.3 Hz, 1 H)

1-{3-Ethyl-2-[3-(4-methyl-piperazin-1-yl)-phenoxy]-pyridin-4-yl}-ethylamine

[Formula 22]

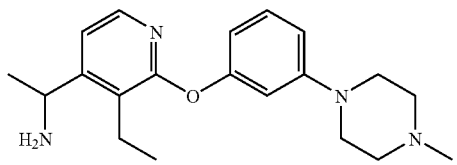

(6) To a solution of the compound obtained in Example 2-(5) (227 mg) in ethanol (5 ml), hydrazine monohydrate (72 mg) was added and refluxed for 2 hours. The reaction mixture was cooled to room temperature, filtered and then concentrated. The resulting crude product was purified by column chromatography (NH-type SiO$_2$, MeOH/CHCl$_3$=0% to 9%) to give the titled compound (146 mg, light-yellow oil).

$^1$H NMR (200 MHz, CDCl$_3$) δ ppm: 1.24 (t, J=7.5 Hz, 3 H), 1.38 (d, J=6.6 Hz, 3 H), 2.34 (s, 3 H), 2.52-2.57 (m, 4 H), 2.70-2.89 (m, 2 H), 3.20-3.24 (m, 4 H), 4.44 (q, J=6.6 Hz, 1 H), 6.53 (dd, J=8.0, 2.2 Hz, 1 H), 6.66 (t, J=2.2 Hz, 1 H), 6.72 (dd, J=8.0, 2.2 Hz, 1 H), 7.12 (d, J=5.3 Hz, 1 H), 7.23 (t, J=8.0 Hz, 1 H), 8.01 (d, J=5.3 Hz, 1 H)

3,4-Dichloro-N-(1-{3-ethyl-2-[3-(4-methyl-piperazin-1-yl)-phenoxy]-pyridin-4-yl}-ethyl)-benzene-sulfonamide (Compound 3)

[Formula 23]

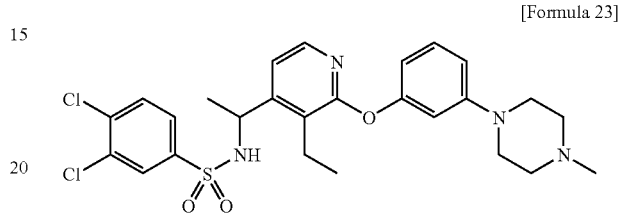

(7) Under a nitrogen atmosphere, to a solution of the compound obtained in Example 2-(6) (146 mg) in THF (3 ml), 3,4-dichlorobenzenesulfonyl chloride (116 mg) and triethylamine (65 mg) were added at 0° C. and stirred at the same temperature for 1 hour. The reaction mixture was filtered and then concentrated. The resulting crude product was purified by column chromatography (NH-type SiO$_2$, MeOH/CHCl$_3$=0% to 5%), followed by recrystallization (AcOEt-hexane) to give the titled compound (Compound 3) (122 mg, colorless powder).

$^1$H NMR (200 MHz, CDCl$_3$) δ ppm: 1.21 (t, J=7.5 Hz, 3 H), 1.46 (d, J=6.59 Hz, 3 H), 2.35 (s, 3 H), 2.53-2.59 (m, 4 H), 2.66-2.79 (m, 2 H), 3.21-3.26 (m, 4 H), 4.90 (quint, J=7.5 Hz, 1 H), 5.04 (brd, J=7.5 Hz, 1 H), 6.50 (dd, J=8.1, 2.2 Hz, 1 H), 6.63 (d, J=5.3 Hz, 1 H), 6.65 (t, J=2.2 Hz, 1 H), 6.75 (dd, J=7.9, 2.2 Hz, 1 H), 7.25 (dd, J=8.1, 7.9 Hz, 1 H), 7.44 (d, J=8.3 Hz, 1 H), 7.50 (dd, J=8.3, 2.2 Hz, 1 H), 7.73 (d, J=2.2 Hz, 1 H), 7.79 (d, J=5.3 Hz, 1 H)

EXAMPLE 3

*3,4-Dichloro-N-(1-{3-ethyl-2-[3-(4-methyl-piperazin-1-yl)-phenoxy]-pyridin-4-yl}-ethyl)-benzene-sulfonamide (Compounds 28 and 29)

[Formula 24]

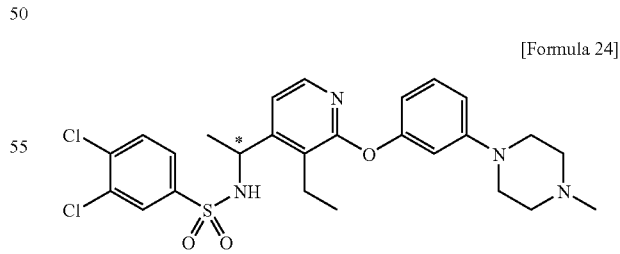

The compound obtained in Example 2 (100 mg) was optically resolved on an optical resolution column (column: CHIRALPAK AD [Daicel Chemical Industries, Ltd., Japan], 2 cmφ×25 cmL; eluent: i-PrOH/hexane=10%, flow rate: 6.0 ml/min) to give the titled compound (Compound 28) [(R)-form, 11 mg, colorless powder, whose configuration was determined by X-ray structural analysis] and another titled compound (Compound 29) [(S)-form, 12 mg, colorless powder, whose configuration was determined by X-ray structural analysis].

(R)-3,4-Dichloro-N-(1-{3-ethyl-2-[3-(4-methyl-piperazin-1-yl)-phenoxy]-pyridin-4-yl}-ethyl)-benzenesulfonamide (Compound 28)

[Formula 25]

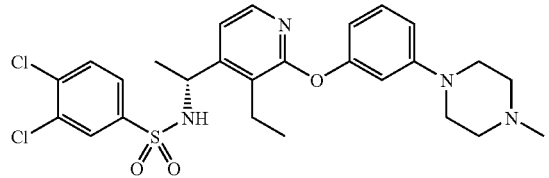

Retention time: 23.0 min (column: CHIRALPAK AD [Daicel Chemical Industries, Ltd., Japan], 4.6 mmφ×250 mL; eluent: i-PrOH/hexane=20%; flow rate: 0.5 ml/min; detect: UV 254 nm)

(S)-3,4-Dichloro-N-(1-{3-ethyl-2-[3-(4-methyl-piperazin-1-yl)-phenoxy]-pyridin-4-yl}-ethyl)-benzenesulfonamide (Compound 29)

[Formula 26]

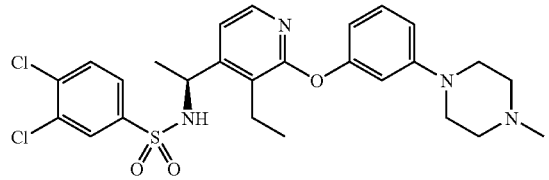

Retention time: 28.9 min (column: CHIRALPAK AD [Daicel Chemical Industries, Ltd., Japan], 4.6 mmφ×250 mL; eluent: i-PrOH/hexane=20%; flow rate: 0.5 ml/min; detect: UV 254 nm)

EXAMPLE 4

5-Chloro-naphthalene-2-sulfonic acid (1-{3-ethyl-4-[3-(4-methyl-piperazin-1-yl)-phenoxy]-pyridin-2-yl}-ethyl)-amide (Compound 4)

[Formula 27]

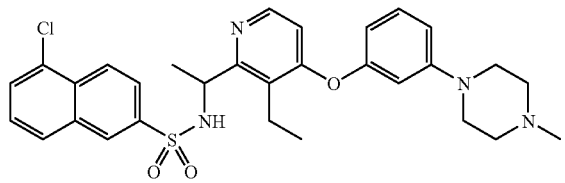

3-Ethyl-4-iodo-pyridine-2-carbonitrile

[Formula 28]

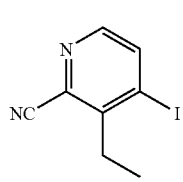

(1) Under a nitrogen atmosphere, to a solution of 3-ethyl-2-fluoro-4-iodo-pyridine obtained in Example 2-(2) (3.425 g) in dimethyl sulfoxide (5 ml), sodium cyanide (668 mg) was added and stirred at 150° C. for 3 hours. The reaction mixture was diluted with a potassium hydroxide solution and extracted with ether. The organic layer was dried over MgSO$_4$, filtered and then evaporated under reduced pressure to remove the solvent. The resulting crude product was purified by column chromatography (acidic OH-type SiO$_2$, AcOEt/hexane=9% to 11%) to give the titled compound (250 mg, yellow oil) and the starting material (1.61 g). To a solution of the collected starting material (1.61 g) in dimethyl sulfoxide (15 ml), potassium cyanide (626 mg) was added and stirred at 150° C. for 3 hours. The reaction mixture was worked up in the same manner to give the titled compound (349 mg, total yield: 599 mg).

$^1$H NMR (200 MHz, CDCl$_3$) δ ppm 1.28 (t, J=7.7 Hz, 3 H), 3.06 (q, J=7.7 Hz, 2 H), 7.96 (d, J=4.8 Hz, 1 H), 8.09 (d, J=4.8 Hz, 1 H)

3-Ethyl-4-[3-(4-methyl-piperazin-1-yl)-phenoxy]-pyridine-2-carbonitrile

[Formula 29]

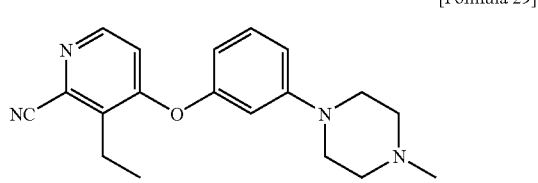

(2) Under a nitrogen atmosphere, to a solution of the compound obtained in Example 4-(1) (599 mg) in dimethylformamide (20 ml), 3-(4-methyl-piperazin-1-yl)-phenol (894 mg), copper powder (74 mg), copper iodide (222 mg) and cesium carbonate (2.273 g) were added and stirred at 150° C. for 1 hour. The reaction mixture was diluted with THF and filtered to remove solids, and the filtrate was evaporated under reduced pressure. The resulting crude product was purified by column chromatography (OH-type SiO$_2$, MeOH/CHCl$_3$=0% to 11%) to give the titled compound (682 mg, yellow oil).

$^1$H NMR (200 MHz, CDCl$_3$) δ ppm 1.32 (t, J=7.5 Hz, 3 H), 2.36 (s, 3 H), 2.54-2.59 (m, 4 H), 3.02 (q, J=7.5 Hz, 2 H), 3.21-3.26 (m, 4 H), 6.50 (dd, J=8.4, 2.2 Hz, 1 H), 6.59 (t, J=2.2 Hz, 1 H), 6.76 (d, J=5.7 Hz, 1 H), 6.82 (dd, J=8.4, 2.2 Hz, 1 H), 7.7 (t, J=8.4 Hz, 1 H), 8.30 (d, J=5.7 Hz, 1 H)

1-{3-Ethyl-4-[3-(4-methyl-piperazin-1-yl)-phenoxy]-pyridin-2-yl}-ethanone

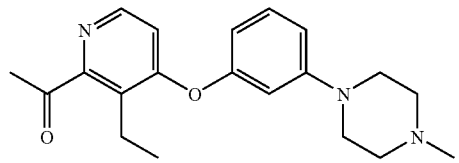

[Formula 30]

(3) Under a nitrogen atmosphere, to a solution of the compound obtained in Example 4-(2) (570 mg) in THF (10 ml), methylmagnesium iodide (2.65 mg, 2 M in ether) was added at room temperature and stirred at the same temperature for 2 hours. To this mixture, aqueous hydrochloric acid (10 ml, 1 M) was added and stirred for 30 minutes at room temperature. The reaction mixture was diluted with aqueous potassium hydroxide and extracted with THF/ether. The organic layer was dried over Na$_2$SO$_4$, filtered and then evaporated under reduced pressure to remove the solvent. The resulting crude product was purified by column chromatography (acidic OH-type SiO$_2$, hexane/CHCl$_3$=50%) to give the titled compound (415 mg, yellow oil).

$^1$H NMR (200 MHz, CDCl$_3$) δ ppm 1.27 (t, J=7.5 Hz, 3 H), 2.35 (s, 3 H), 2.54-2.59 (m, 4 H), 2.70 (s, 3 H), 3.00 (q, J=7.5 Hz, 2 H), 3.20-3.25 (m, 4H), 6.51 (dd, J=8.4, 2.2 Hz, 1 H), 6.60 (t, J=2.2 Hz, 1 H), 6.73 (d, J=5.3 Hz, 1H), 6.78 (dd, J=8.4, 2.2 Hz, 1 H), 7.27 (t, J=8.4 Hz, 1 H), 8.27 (d, J=5.3 Hz, 1 H)

1-{3-Ethyl-4-[3-(4-methyl-piperazin-1-yl)-phenoxy]-pyridin-2-yl}-ethanol

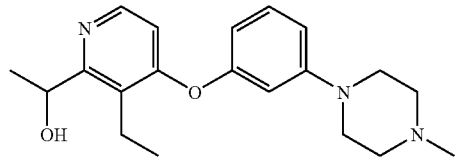

[Formula 31]

(4) To a solution of the compound obtained in Example 4-(3) (415 mg) in ethanol (10 ml), sodium tetrahydroborate (93 mg) was added at room temperature and stirred at the same temperature for 1 hour. The reaction mixture was diluted with a potassium hydroxide solution and extracted with THF/ether. The organic layer was dried over Na$_2$SO$_4$, filtered and then evaporated under reduced pressure to remove the solvent. The resulting crude product was purified by column chromatography (NH-type SiO$_2$, hexane/CHCl$_3$=33%) to give the titled compound (371 mg, light-yellow oil).

$^1$H NMR (200 MHz, CDCl$_3$) δ ppm 1.23 (t, J=7.5 Hz, 3 H), 1.46 (d, J=6.2 Hz, 3 H), 2.35 (s, 3 H), 2.54-2.59 (m, 4 H), 2.62-2.85 (m, 2 H), 3.20-3.25 (m, 4 H), 5.05 (q, J=6.2 Hz, 1 H), 6.51 (dd, J=8.4, 2.2 Hz, 1 H), 6.56 (d, J=5.7 Hz, 1 H), 6.60 (t, J=2.2 Hz, 1 H), 6.77 (dd, J=8.4, 2.2 Hz, 1 H), 7.27 (t, J=8.4 Hz, 1 H), 8.21 (d, J=5.7 Hz, 1 H)

2-(1-{3-Ethyl-4-[3-(4-methyl-piperazin-1-yl)-phenoxy]-pyridin-2-yl}-ethyl)-isoindole-1,3-dione

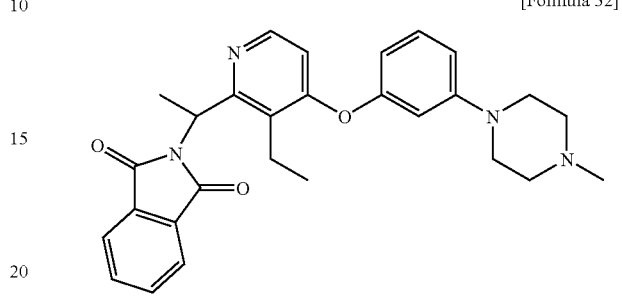

[Formula 32]

(5) Under a nitrogen atmosphere, to a solution of the compound obtained in Example 4-(4) (371 mg), triphenylphosphine (428 mg) and phthalimide (208 mg) in THF (5 ml), diethyl azodicarboxylate (DEAD, 710 mg, 40% in toluene) was added at 0° C. and stirred at the same temperature for 1 hour. The reaction mixture was concentrated, and the resulting crude product was purified by column chromatography (NH-type SiO$_2$, CHCl$_3$) to give the titled compound (467 mg, yellow oil).

$^1$H NMR (200 MHz, CDCl$_3$) δ ppm 1.19 (t, J=7.5 Hz, 3 H), 1.96 (d, J=7.5 Hz, 3 H), 2.34 (s, 3 H), 2.53-2.58 (m, 4 H), 2.65-2.97 (m, 2 H), 3.18-3.23 (m, 2 H), 5.81 (q, J=7.5 Hz, 1 H), 6.49 (dd, J=8.4, 2.2 Hz, 1 H), 6.55 (d, J=5.3 Hz, 1 H), 6.57 (t, J=2.2 Hz, 1 H), 6.75 (dd, J=8.4, 2.2 Hz, 1 H), 7.25 (t, J=8.4 Hz, 1 H), 7.67-7.72 (m, 2 H), 7.81-7.85 (m, 2 H), 8.25 (d, J=5.3 Hz, 1 H)

1-{3-Ethyl-4-[3-(4-methyl-piperazin-1-yl)-phenoxy]-pyridin-2-yl}-ethylamine

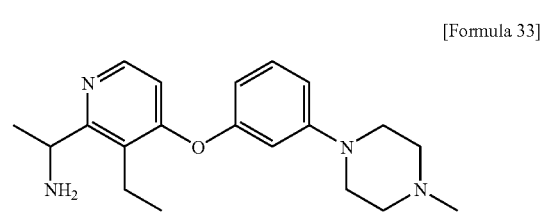

[Formula 33]

(6) To a solution of the compound obtained in Example 4-(5) (467 mg) in ethanol (5 ml), hydrazine monohydrate (149 mg) was added at room temperature and refluxed for 1 hour. The reaction mixture was concentrated, and the resulting crude product was purified by column chromatography (NH-type SiO$_2$, MeOH/CHCl$_3$=0% to 11%) to give the titled compound (249 mg, yellow oil).

$^1$H NMR (200 MHz, CDCl$_3$) δ ppm 1.23 (t, J=7.0 Hz, 3 H), 1.42 (d, J=6.6 Hz, 3 H), 2.34-2.35 (m, 3 H), 2.54-2.58 (m, 4 H), 2.69-2.90 (m, 2 H), 3.19-3.25 (m, 4 H), 4.37 (q, J=6.6 Hz, 1 H), 6.48 (dd, J=8.4, 2.2 Hz, 1 H), 6.51 (d, J=5.7 Hz, 1 H), 6.60 (t, J=2.2 Hz, 1 H), 6.76 (dd, J=8.4, 2.2 Hz, 1 H), 7.25 (t, J=8.4 Hz, 1 H), 8.25 (d, J=5.7 Hz, 1 H)

5-Chloro-naphthalene-2-sulfonic acid (1-{3-ethyl-4-[3-(4-methyl-piperazin-1-yl)-phenoxy]-pyridin-2-yl}-ethyl)-amide (Compound 4)

[Formula 34]

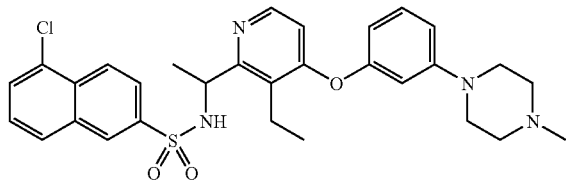

(7) To a solution of the compound obtained in Example 4-(6) (100 mg) in THF (5 ml), 5-chloro-2-naphthalenesulfonyl chloride (84 mg) and triethylamine (45 mg) were added at room temperature and stirred at the same temperature for 1 hour. The reaction mixture was concentrated, and the resulting crude product was purified by column chromatography (acidic OH-type SiO$_2$, CHCl$_3$), followed by recrystallization (ether-hexane) to give the titled compound (54 mg, colorless powder).
$^1$H NMR (200 MHz, CDCl$_3$) δ ppm 0.97 (t, J=7.3 Hz, 3 H), 1.44 (d, J=6.6 Hz, 3 H), 2.36 (s, 3 H), 2.55-2.60 (m, 4 H), 3.18-3.23 (m, 4 H), 4.74-4.88 (m, 1 H), 6.10 (dd, J=8.4, 1.0 Hz, 1 H), 6.20 (d, J=5.7 Hz, 1 H), 6.42-6.44 (m, 1 H), 6.55 (d, J=8.8 Hz, 1 H), 6.73 (dd, J=8.4, 1.0 Hz, 1 H), 7.18 (t, J=8.4 Hz, 1 H), 7.46 (t, J=8.4 Hz, 1 H), 7.65-7.79 (m, 3H), 7.95 (d, J=5.7 Hz, 1 H), 8.12 (d, J=9.2 Hz, 1 H), 8.28 (s, 1 H)

EXAMPLE 5

3,4-Dichloro-N-[1-(2-isopropoxy-3-ethyl-pyridin-4-yl)-ethyl]-benzenesulfonamide (Compound 26)

[Formula 35]

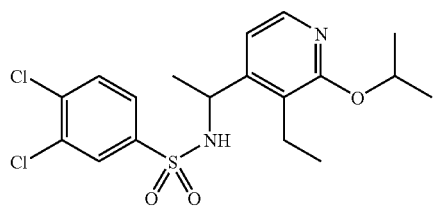

3-Ethyl-2-fluoro-pyridine-4-carbaldehyde

[Formula 36]

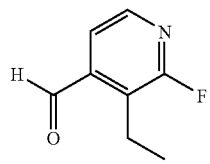

(1) Under a nitrogen atmosphere, to a solution of 3-ethyl-2-fluoro-4-iodo-pyridine obtained in Example 2-(2) (3.45 g) in THF (35 ml), isopropylmagnesium chloride (7.6 ml, 2.0 M in THF) was added at room temperature and stirred at 45° C. for 2 hours. To the reaction mixture, dimethylformamide (2.1 ml) was added and stirred overnight at room temperature. The reaction mixture was diluted with water and extracted with AcOEt. The resulting organic layer was washed with brine, dried over MgSO$_4$, filtered and then evaporated under reduced pressure to remove the solvent. The resulting crude product was purified by column chromatography (OH-type SiO$_2$, AcOEt/hexane=0% to 50%) to give the titled compound (1.71 g, colorless oil).
$^1$H NMR (600 MHz CDCl$_3$) δ ppm: 1.29 (t, J=7.7 Hz, 3H), 3.06 (q, J=7.7 Hz, 2 H), 7.53-7.57 (m, 1H), 8.25-8.28 (m, 1H), 10.36 (s, 1H)

1-(3-Ethyl-2-fluoro-pyridin-4-yl)-ethanol

[Formula 37]

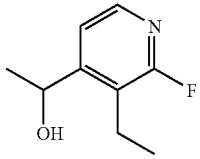

(2) To a solution of the compound obtained in Example 5-(1) (1.00 g) in THF (10 ml), MeMgBr (0.75 ml, 3.0 mmol, in Et$_2$O) was added at 0° C. under a nitrogen atmosphere and stirred at 0° C. for 2 hours. The reaction mixture was diluted with water and extracted with AcOEt. The resulting organic layer was washed with brine, dried over MgSO$_4$, filtered and then evaporated under reduced pressure to remove the solvent. The resulting crude product was purified by column chromatography (OH-type SiO$_2$, AcOEt/hexane=0% to 50%) to give the titled compound (1.05 g, colorless oil).
$^1$H NMR (600 MHz, CDCl$_3$) δ ppm: 1.21 (t, J=7.6 Hz, 3H), 1.49 (d, J=6.4 Hz, 3H), 2.58-2.74 (m, 2H), 5.17 (q, J=6.4 Hz, 1H), 7.34-7.38 (m, 1H), 8.03-8.08 (m, 1H)

2-[1-(3-Ethyl-2-fluoro-pyridin-4-yl)-ethyl]-isoindole-1,3-dione

[Formula 38]

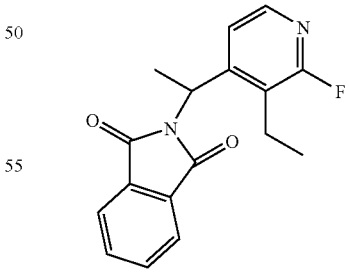

(3) Under a nitrogen atmosphere, to a solution of the compound obtained in Example 5-(2) (1.05 g) in THF (5 ml), triphenylphosphine (2.30 g), phthalimide (1.10 g) and diethyl azodicarboxylate (DEAD, 3.76 ml, 2 M in toluene) were added at room temperature and stirred at the same temperature for 2 hours. The reaction mixture was concentrated, and the resulting crude product was purified by column chromatography (acidic SiO$_2$, AcOEt/hexane=0% to 40%) to give the titled compound (1.43 g, yellow solid).

$^1$H NMR (600 MHz, CDCl$_3$) δ ppm: 1.15 (t, J=7.6 Hz, 3H), 1.89 (d, J=7.1 Hz, 3H), 2.67-2.88 (m, 2H), 5.73 (q, J=7.1 Hz, 1H), 7.58-7.63 (m, 1H), 7.71-7.75 (m, 2H), 7.81-7.86 (m, 2H), 8.03-8.07 (m, 1H)

1-(3-Ethyl-2-fluoro-pyridin-4-yl)-ethylamine

[Formula 39]

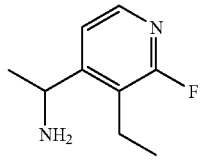

(4) To a solution of the compound obtained in Example 5-(3) (1.43 g) in ethanol (20 ml), hydrazine monohydrate (0.7 ml) was added and stirred overnight at room temperature. The reaction mixture was concentrated, and the resulting crude product was purified by column chromatography (NH-type SiO$_2$, AcOEt/hexane=0% to 99%) to give the titled compound (535 mg, colorless oil).

$^1$H NMR (600 MHz, CDCl$_3$) δ ppm: 1.20 (t, J=7.6 Hz, 3H), 1.36 (d, J=6.4 Hz, 3H), 2.64-2.78 (m, 2H), 4.42 (q, J=6.4 Hz, 1H), 7.30-7.36 (m, 1H), 8.00-8.05 (m, 1H)

1-(3-Ethyl-2-4-yl)-ethylamine

[Formula 40]

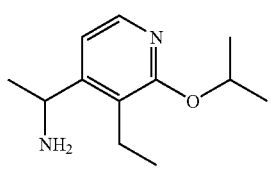

(5) A mixture of the compound obtained in Example 5-(4) (200 mg), isopropanol (0.5 ml), Cs$_2$CO$_3$ (775 mg) and N,N'-dimethylpropyleneurea (DMPU) (1.0 ml) was stirred at 200° C. for 3 hours. After cooling to room temperature, CHCl$_3$ and hydrochloric acid (1.0 N) were added, and the aqueous layer was extracted with CHCl$_3$, alkalinized with NaOH and further extracted with CHCl$_3$. The organic layer was dried over MgSO$_4$, filtered and then evaporated under reduced pressure to remove the solvent, thereby giving the titled compound (213 mg, colorless oil).

$^1$H NMR (600 MHz, CDCl$_3$) δ ppm: 1.12 (t, J=7.6 Hz, 3H), 1.32-1.38 (m, 9H), 2.59-2.69 (m, 2H), 4.35 (q, J=6.4 Hz, 1H), 5.28-5.36 (m, 1H), 6.92-6.95 (m, 1H), 7.96-8.00 (m, 1H)

3,4-Dichloro-N-[1-(2-isopropoxy-3-ethyl-pyridin-4-yl)-ethyl]-benzenesulfonamide (Compound 26)

[Formula 41]

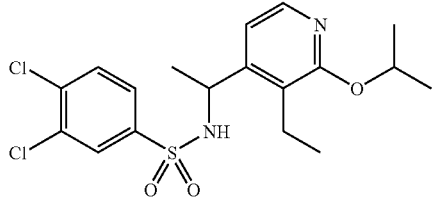

(6) Under a nitrogen atmosphere, to a solution of the compound obtained in Example 5-(5) (150 mg) in THF (2 ml), 3,4-dichlorobenzenesulfonyl chloride (212 mg) and triethylamine (0.2 ml) were added at 0° C. and stirred at the same temperature for 2 hours. The reaction mixture was filtered and then concentrated. The resulting crude product was purified by column chromatography (NH-type SiO$_2$, AcOEt/hexane=0% to 50%), followed by recrystallization (AcOEt-hexane) to give the titled compound (62 mg, colorless powder).

$^1$H NMR (600 MHz, CDCl$_3$) δ ppm: 1.03-1.11 (m, 3H), 1.29-1.36 (m, 6H), 1.42 (d, J=6.4 Hz, 3H), 2.47-2.60 (m, 2H), 4.77-4.85 (m, 1H), 4.85-4.90 (m, 1H), 5.20-5.29 (m, 1H), 6.40-6.43 (m, 1H), 7.37-7.40 (m, 1H), 7.42-7.46 (m, 1H), 7.64-7.67 (m, 1H), 7.73-7.77 (m, 1H)

EXAMPLE 6

5-Chloronaphthalene-2-sulfonic acid [1-(3-ethyl-2-p-toluylsulfanyl-pyridin-4-yl)-ethyl]-amide (Compound 58)

[Formula 42]

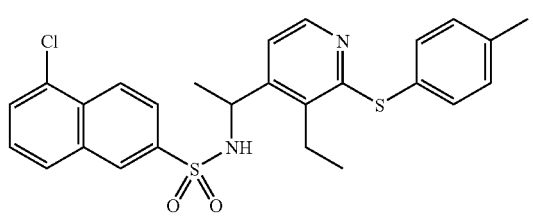

1-(3-Ethyl-2-p-toluylsulfanyl-pyridin-4-yl)-ethylamine

[Formula 43]

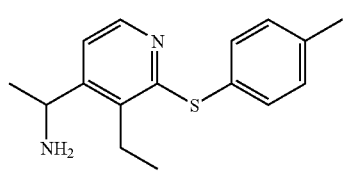

(1) Into a pressure-resistant screw-capped test tube, the compound obtained in Example 5-(4) (500 mg), DMPU (1.0 mL), 4-methylbenzenethiol (443 mg) and cesium carbonate (1.94 g) were introduced and stirred at 200° C. for 2 hours. After cooling to room temperature, CHCl$_3$ and hydrochloric acid (1.0 N) were added, and the aqueous layer was extracted with CHCl$_3$, alkalinized with NaOH and then extracted with CHCl$_3$. The organic layer was dried over MgSO$_4$, filtered and then evaporated under reduced pressure to remove the solvent, thereby giving the titled compound (601 mg, light-yellow solid).

$^1$H NMR (600 MHz, CDCl$_3$) δ ppm 1.27 (t, J=7.6 Hz, 3H), 1.36 (d, J=6.8 Hz, 3H), 2.36 (s, 3H), 2.79-2.94 (m, 2H), 4.39 (q, J=6.8 Hz, 1H), 7.15-7.21 (m, 3H), 7.37-7.42 (m, 2H), 8.18-8.22 (m, 1H)

5-Chloronaphthalene-2-sulfonic acid [1-(3-ethyl-2-p-toluylsulfanyl-pyridin-4-yl)-ethyl]-amide (Compound 58)

[Formula 44]

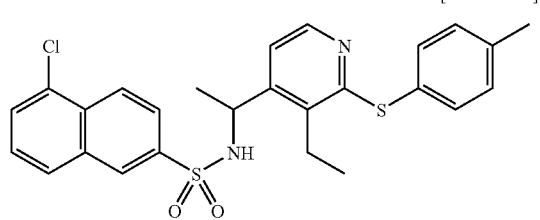

(2) To a solution of the compound obtained in Example 6-(1) (302 mg) in THF (5.0 ml), 5-chloro-2-naphthalenesulfonyl chloride (284 mg) and triethylamine (310 μl) were added at room temperature and stirred at the same temperature for 1 hour. The reaction mixture was concentrated, and the resulting crude product was purified by column chromatography (NH-type SiO$_2$, AcOEt/hexane=10%), followed by recrystallization (ether-hexane) to give the titled compound (385 mg, colorless powder).

$^1$H NMR (600 MHz, CDCl$_3$) δ ppm: 1.20 (t, J=7.6 Hz, 3H), 1.41 (d, J=6.9 Hz, 3H), 2.36 (s, 3H), 2.63-2.89 (m, 2H), 4.82-4.91 (m, 1H), 4.95-5.02 (m, 1H), 6.64-6.68 (m, 1H), 7.14-7.19 (m, 2H), 7.22-7.25 (m, 2H), 7.48-7.53 (m, 1H), 7.70-7.82 (m, 4H), 8.18-8.22 (m, 1H), 8.24-8.28 (m, 1H)

EXAMPLE 7

5-Chloronaphthalene-2-sulfonic acid {1-[3-ethyl-2-(toluene-4-sulfonyl)-pyridin-4-yl]-ethyl}-amide (Compound 59)

[Formula 45]

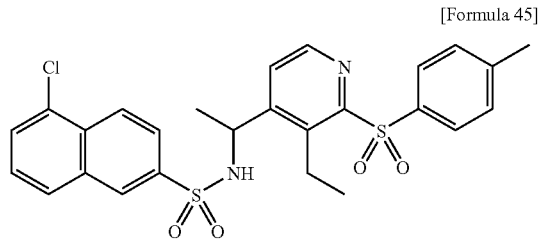

To a solution of the compound obtained in Example 6-(2) (150 mg) in chloroform (6.0 mL), m-chloroperbenzoic acid (535 mg) was added and stirred overnight at room temperature. The reaction mixture was diluted with a 5% aqueous Na$_2$S$_2$O$_3$ solution and extracted with chloroform. The organic layer was washed with brine and dried over anhydrous magnesium sulfate. After filtration, the solvent was distilled off under reduced pressure, and the resulting crude product was purified by column chromatography (NH-type SiO$_2$, AcOEt/hexane=0% to 100%, MeOH/CHCl$_3$=0% to 10%) to give the titled compound (Compound 59) (colorless powdery compound, 116 mg).

$^1$H NMR (600 MHz, CDCl$_3$) δ ppm: 1.33 (t, J=7.6 Hz, 3H), 1.41 (d, J=6.9 Hz, 3H), 2.46 (s, 3H), 3.06-3.40 (m, 2H), 4.93-4.99 (m, 1H), 5.00-5.05 (m, 1H), 7.06-7.09 (m, 1H), 7.31-7.36 (m, 2H), 7.50-7.56 (m, 1H), 7.66-7.84 (m, 6H), 8.12-8.16 (m, 1H), 8.24-8.29 (m, 1H)

EXAMPLE 8

5-Chloronaphthalene-2-sulfonic acid {1-[3-ethyl-2-(3-morpholin-4-yl-phenoxy)-pyridin-4-yl]-ethyl}-methyl-amide (Compound 60)

[Formula 46]

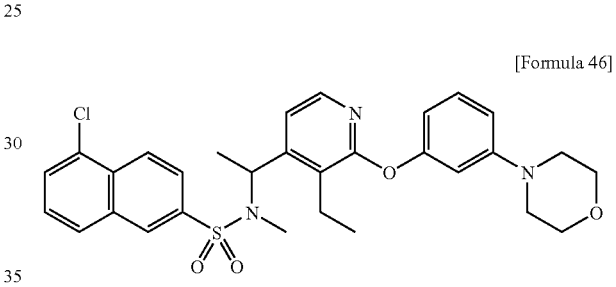

5-Chloronaphthalene-2-sulfonic acid {1-[3-ethyl-2-(3-morpholin-4-yl-phenoxy)-pyridin-4-yl]-ethyl}-amide (Compound 27)

[Formula 47]

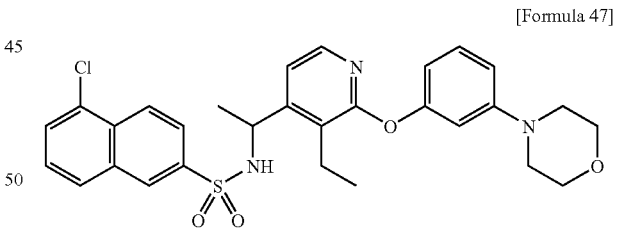

(1) 1-[3-Ethyl-2-(3-morpholin-4-yl-phenoxy)-pyridin-4-yl]-ethylamine (168 mg), which had been obtained in the same manner as shown in Example 5-(4), except that isopropanol in Example 5-(4) was replaced by 3-morpholinophenol, was dissolved in THF (2 ml). To this solution, 5-chloro-2-naphthalenesulfonyl chloride (156 mg) and triethylamine (140 μl) were added at room temperature and stirred overnight at the same temperature. The reaction mixture was concentrated, and the resulting crude product was purified by column chromatography (NH-type SiO$_2$, AcOEt/hexane=10% to 99%), followed by recrystallization (EtOH) to give the titled compound (127 mg, colorless powder).

$^1$H NMR (600 MHz, CDCl$_3$) δ ppm: 1.16 (t, J=7.6 Hz, 3H), 1.43 (d, J=6.9 Hz, 3H), 2.58-2.77 (m, 2H), 3.12-3.18 (m, 4H), 3.82-3.86 (m, 4H), 4.87-4.94 (m, 1H), 4.94-4.99 (m, 1H), 6.32-6.36 (m, 1H), 6.53-6.57 (m, 1H), 6.66-6.73 (m, 2H), 7.20-7.24 (m, 1H), 7.48-7.53 (m, 1H), 7.67-7.73 (m, 2H), 7.78-7.82 (m, 2H), 8.25-8.32 (m, 2H)

5-Chloronaphthalene-2-sulfonic acid {1-[3-ethyl-2-(3-morpholin-4-yl-phenoxy)-pyridin-4-yl]-ethyl}-methyl-amide (Compound 60)

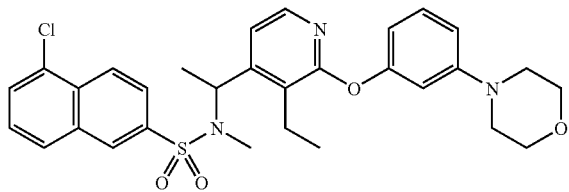

[Formula 48]

(2) To a solution of the compound obtained in Example 8-(1) (50 mg) in DMF (0.5 ml), $K_2CO_3$ (25 mg) and MeI (7 μl) were added and stirred at room temperature for 3 days. The reaction mixture was diluted with water and extracted with chloroform. The resulting organic layer was washed with brine, dried over $MgSO_4$, filtered and then concentrated. The resulting crude product was purified by column chromatography (NH-type $SiO_2$, AcOEt/hexane=0% to 50%), followed by recrystallization ($Et_2O$-hexane) to give the titled compound (Compound 60) (29 mg, colorless powder).

$^1$H NMR (600 MHz, CDCl$_3$) δ ppm: 1.30 (t, J=7.6 Hz, 3H), 1.33 (d, J=7.3 Hz, 3H), 2.75 (s, 3H), 2.95-3.07 (m, 2H), 3.14-3.21 (m, 4H), 3.80-3.87 (m, 4H), 5.61-5.69 (m, 1H), 6.54-6.58 (m, 1H), 6.64-6.66 (m, 1H), 6.71-6.75 (m, 1H), 6.81-6.84 (m, 1H), 7.24-7.29 (m, 1H), 7.52-7.57 (m, 1H), 7.72-7.77 (m, 1H), 7.87-7.95 (m, 3H), 8.38-8.43 (m, 2 H)

Starting from corresponding starting materials, the same procedures as shown in Examples 1 to 8 were repeated, followed by salt formation as needed to obtain the compounds shown in Table 1 below.

The compounds obtained in the above examples are also shown in Table 1, along with other compounds.

The following compounds were obtained from Compound 31 by optical resolution in the same manner as shown in Example 3. Data of their retention time on a chiral column are shown below.

Compound 61: retention time: 12.1 min (column: CHIRAL-PAK AD [Daicel Chemical Industries, Ltd., Japan], 4.6 mmφ×250 mL; eluent: i-PrOH/hexane=30%; flow rate: 0.5 ml/min; detect: UV 254 nm)

Compound 62: retention time: 17.7 min (column: CHIRAL-PAK AD [Daicel Chemical Industries, Ltd., Japan], 4.6 mmφ×250 mL; eluent: i-PrOH/hexane=30%; flow rate: 0.5 ml/min; detect: UV 254 nm)

With respect to the following compounds, $^1$H-NMR data are shown.

Compound 63: (600 MHz, CDCl$_3$) δ ppm: 1.09 (t, J=7.6 Hz, 3H), 1.42 (d, J=6.9 Hz, 3H), 2.01-2.09 (m, 2H), 2.50-2.70 (m, 2H), 3.37 (s, 3H), 3.56 (t, J=6.4 Hz, 2H), 4.30-4.39 (m, 2H), 4.78-4.86 (m, 1H), 4.90-5.08 (m, 1H), 6.44-6.48 (m, 1H), 7.37-7.42 (m, 1H), 7.42-7.47 (m, 1H), 7.63-7.65 (m, 1H), 7.74-7.78 (m, 1H)

Compound 64: (600 MHz, CDCl$_3$) δ ppm: 1.09 (t, J=7.6 Hz, 3H), 1.36-1.43 (m, 5H), 1.44-1.55 (m, 4H), 1.74-1.82 (m, 2H), 2.23 (s, 6H), 2.25-2.30 (m, 2H), 2.51-2.63 (m, 2H), 4.24 (t, J=6.7 Hz, 2H), 4.81 (q, J=6.9 Hz, 1H), 6.48-6.52 (m, 1H), 7.37-7.40 (m, 1H), 7.44-7.47 (m, 1H), 7.64-7.66 (m, 1H), 7.73-7.76 (m, 1H)

Compound 65: (600 MHz, CDCl$_3$) δ ppm: 1.09 (t, J=7.6 Hz, 3H), 1.42 (d, J=6.9 Hz, 3H), 1.89-2.06 (m, 2 H), 2.35-2.71 (m, 8H), 3.70-3.79 (m, 4H), 4.26-4.34 (m, 2H), 4.74-4.86 (m, 1H), 5.53 (br s, 1H), 6.48-6.56 (m, 1H), 7.36-7.42 (m, 1H), 7.44-7.47 (m, 1H), 7.63-7.65 (m, 1H), 7.72-7.76 (m, 1H)

TABLE 1

| Compound No. | Structural formula | Melting point (° C.) |
| --- | --- | --- |
| 1 | | 105.0-106.5 |
| 2 | | 151.0-153.0 |

TABLE 1-continued

| | Structure | mp (°C) |
|---|---|---|
| 3 | 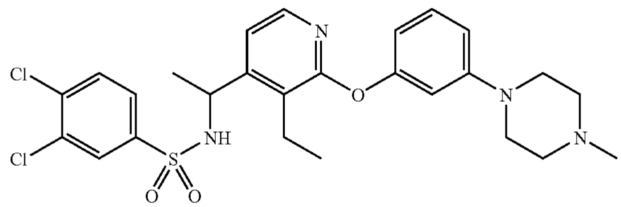 | 165.0-166.0 |
| 4 | 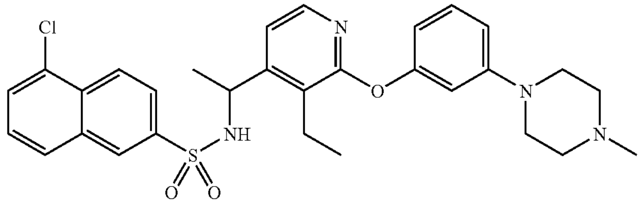 | 155.0-156.0 |
| 5 | 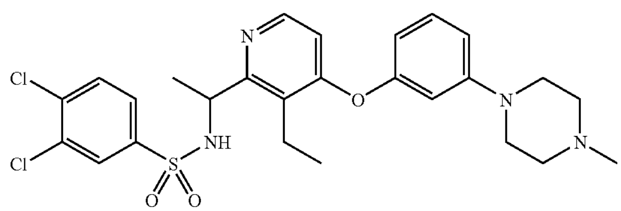 | 134.0-135.0 |
| 6 | 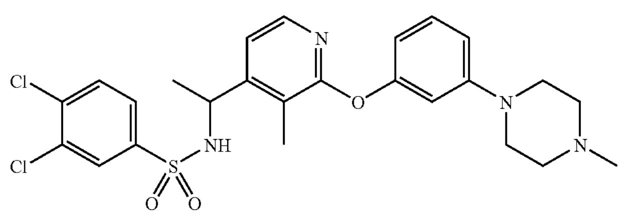 | 163.0-164.5 |
| 7 | 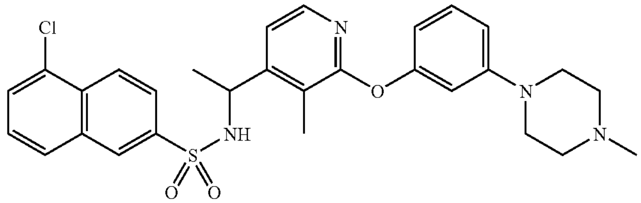 | 185.0-186.0 |
| 8 | 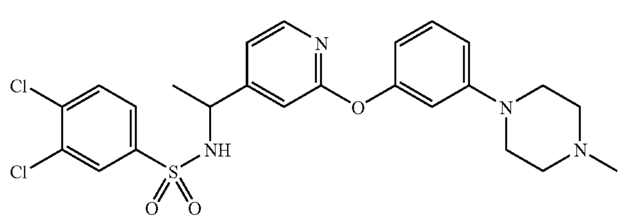 | 157.0-158.0 |
| 9 | 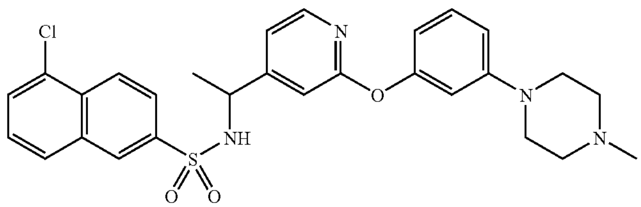 | 178.0-181.0 |

TABLE 1-continued

| # | Structure | mp (°C) |
|---|---|---|
| 10 | (structure) | 168.5-170.0 |
| 11 | (structure) | 160.5-162.0 |
| 12 | (structure) | 153.5-154.5 |
| 13 | (structure) | 146.0-147.0 |
| 14 | (structure) | 182.0-183.0 |
| 15 | (structure) | 188.0-190.0 |
| 16 | (structure) | 122.5-123.5 |

TABLE 1-continued
| 17 | 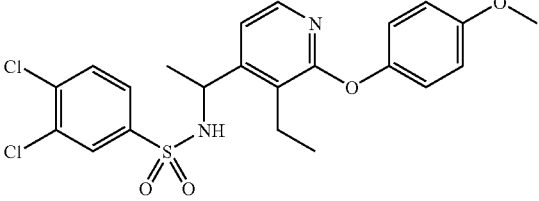 | 130.0-131.0 |
| --- | --- | --- |
| 18 | 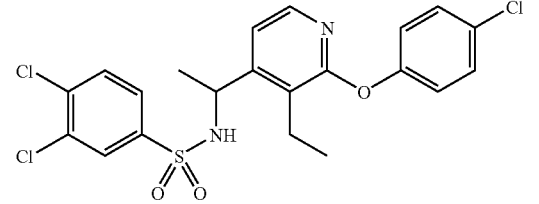 | 138.0-139.0 |
| 19 | 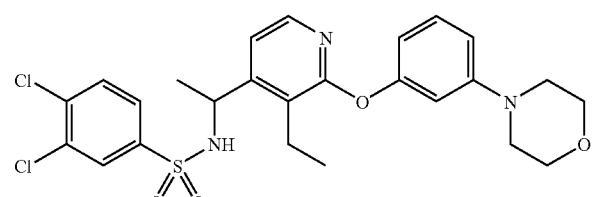 | 132.0-133.0 |
| 20 | 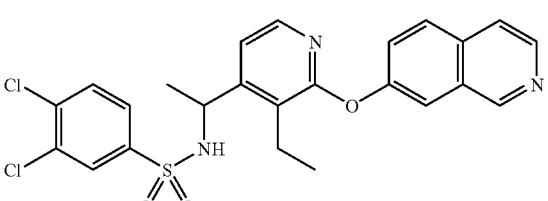 | 120.0-125.0 |
| 21 |  | 145.5-146.5 |
| 22 | 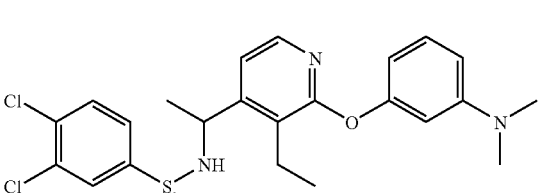 | 169.0-170.0 |
| 23 | 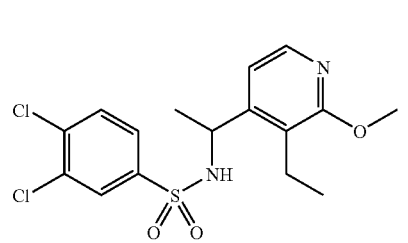 | 145.0-146.0 |

TABLE 1-continued

| # | Structure | mp (°C) |
|---|---|---|
| 24 | 3,4-dichloro-N-(1-(3-ethyl-2-(2,2,2-trifluoroethoxy)pyridin-4-yl)ethyl)benzenesulfonamide | 99.0–100.0 |
| 25 | N-(1-(2-(benzyloxy)-3-ethylpyridin-4-yl)ethyl)-3,4-dichlorobenzenesulfonamide | 125.0–126.0 |
| 26 | 3,4-dichloro-N-(1-(3-ethyl-2-isopropoxypyridin-4-yl)ethyl)benzenesulfonamide | 129.0–131.0 |
| 27 | 5-chloro-N-(1-(3-ethyl-2-(3-morpholinophenoxy)pyridin-4-yl)ethyl)naphthalene-2-sulfonamide | 181.0–183.0 |
| 28 | (S)-3,4-dichloro-N-(1-(3-ethyl-2-(3-(4-methylpiperazin-1-yl)phenoxy)pyridin-4-yl)ethyl)benzenesulfonamide | |
| 29 | (R)-3,4-dichloro-N-(1-(3-ethyl-2-(3-(4-methylpiperazin-1-yl)phenoxy)pyridin-4-yl)ethyl)benzenesulfonamide | |
| 30 | N-(1-(2-cyclobutoxy-3-ethylpyridin-4-yl)ethyl)-3,4-dichlorobenzenesulfonamide | 116.0–117.0 |

Note: Compound names above are illustrative interpretations of the drawn structures; the original table shows only structural diagrams and melting point ranges.

TABLE 1-continued
| | | |
|---|---|---|
| 31 | 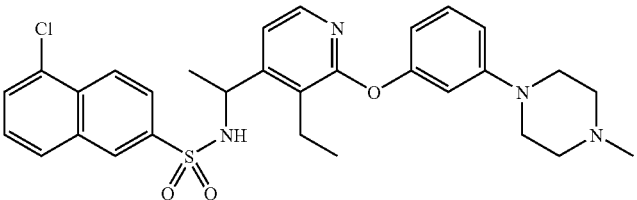 | 159.5-160.5 |
| 32 | 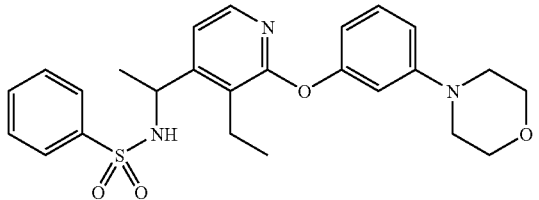 | 170.0-171.0 |
| 33 | 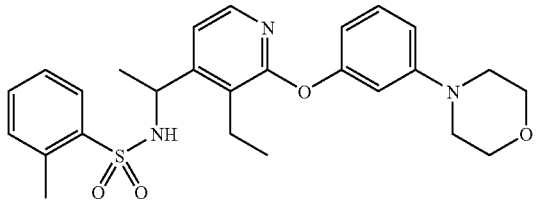 | 190.0-192.0 |
| 34 | 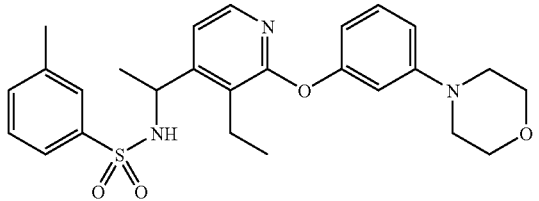 | 148.5-149.5 |
| 35 | 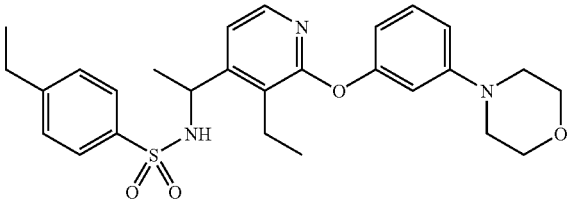 | 120.0-121.0 |
| 36 | 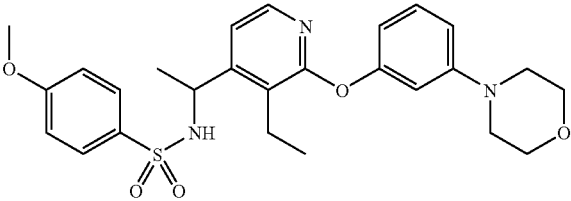 | 147.5-148.5 |
| 37 | 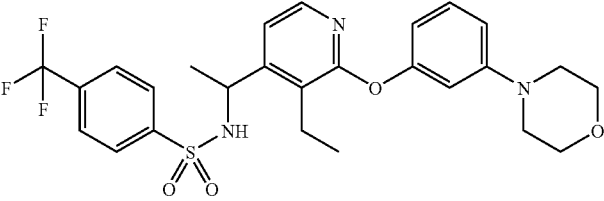 | 123.0-125.0 |

TABLE 1-continued
| | | |
|---|---|---|
| 38 | 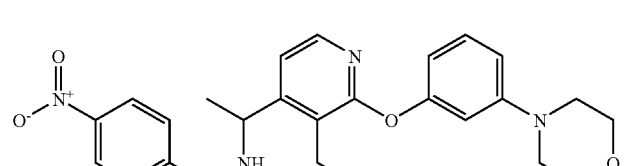 | 114.5-115.5 |
| 39 | 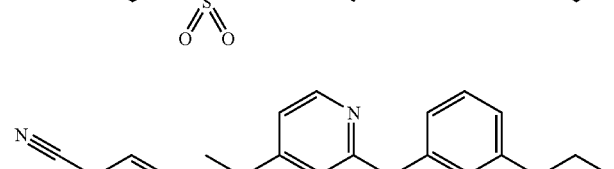 | 195.0-196.0 |
| 40 | 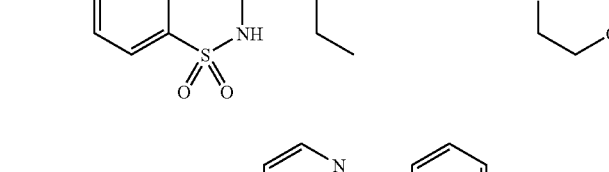 | 104.0-105.0 |
| 41 | 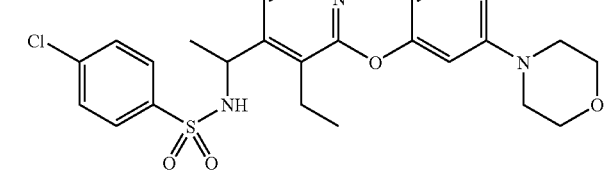 | 175.5-176.5 |
| 42 | 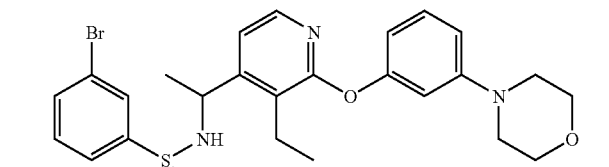 | 157.0-158.5 |
| 43 | 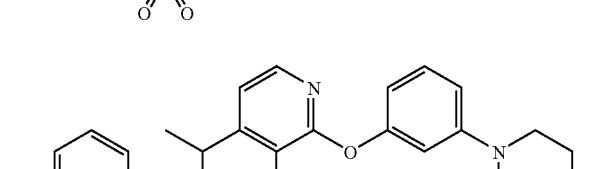 | 198.0-199.0 |
| 44 | 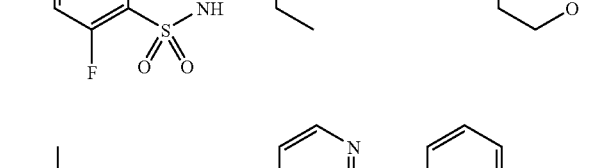 | 164.5-165.5 |

TABLE 1-continued
| 45 | 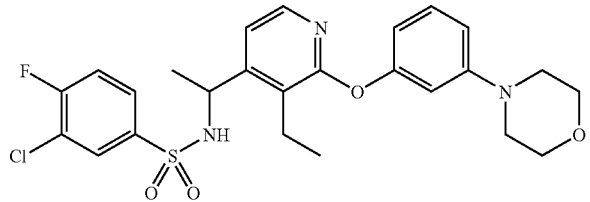 | 134.0-135.0 |
| 46 | 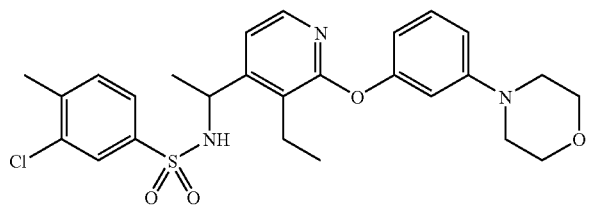 | 147.0-148.0 |
| 47 | 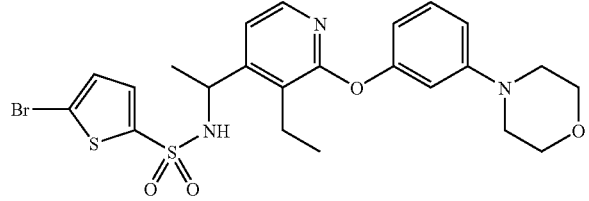 | 146.5-147.5 |
| 48 | 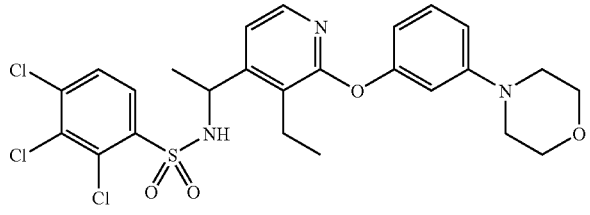 | 133.0-134.0 |
| 49 | 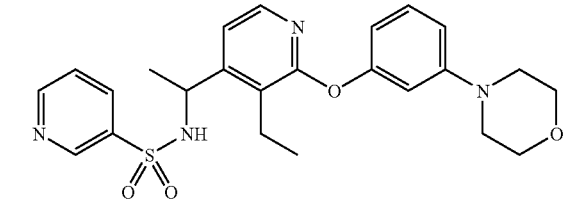 | 185.5-186.5 |
| 50 | 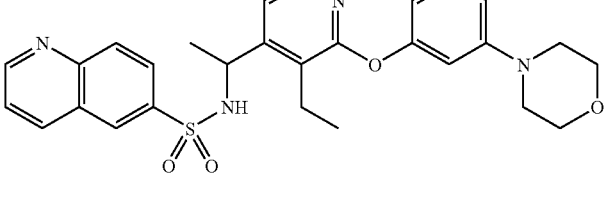 | 149.5-150.5 |
| 51 | 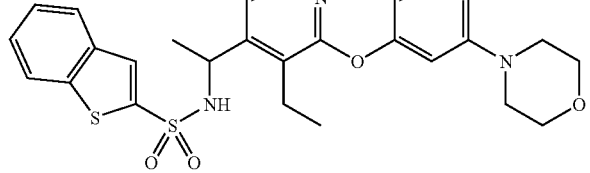 | 89.0-99.0 |

TABLE 1-continued

| | | |
|---|---|---|
| 52 | (structure) | 168.0-169.5 |
| 53 | (structure) | 133.0-133.5 |
| 54 | (structure) | 154.5-156.0 |
| 55 | (structure) | 166.5-167.5 |
| 56 | (structure) | 102.0-104.0 |
| 57 | (structure) | 143.5-145.5 |
| 58 | (structure) | 157.0-158.0 |

TABLE 1-continued

| | | |
|---|---|---|
| 59 | [structure] | 233.0-235.0 |
| 60 | [structure] | 159.0-161.0 |

| Compound No. | Structural formula |
|---|---|
| 61 | [structure] |
| 62 | [structure] |
| 63 | [structure] |
| 64 | [structure] |
| 65 | [structure] |

TEST EXAMPLE 1

S1P₁ Binding Test

The membrane fraction of a HEK-293 cell line carrying the human Edg-1($S1P_1$) gene was used to study the compounds of the present invention for their inhibitory effect on Edg-1 ($S1P_1$) binding, as described in Science. 2002, 296: 346 (Kd=0.15 nM and Bmax=2.5 fmol/μg for binding to [$^{33}$P]-S1P). To obtain the membrane fraction, treatment with solubilizing buffer (1 mM Tris/HCl, pH 7.2) for 10 minutes on ice was performed, followed by centrifugation at 1000×g for 5 minutes to remove an insoluble fraction and then at 40000×g for 30 minutes at 4° C. The resulting membrane fraction was dissolved in binding buffer (20 mM Tris-HCl, pH 7.4, 100 mM NaCl, 15 mM NaF, 2 mM deoxypyridoxine, 4 mg/mL fatty acid-free BSA), followed by addition of binding buffer containing [$^{33}$P]-S1P (ARC, final concentration: 0.1 nM) and DMSO solution of a test compound (final concentration of the compound: $10^{-5}$ M, final concentration of DMSO: 0.1%). After stirring, the reaction solution was incubated at 30° C. for 1 hour. The membrane fraction was collected onto a unifilter-96 GF/C filter (Perkin Elmer) using a harvester and washed four times with binding buffer, followed by drying the filter. After addition of 25 μL Microscint 0 (Perkin Elmer), radioactivity was measured with a Top Count NXT (Packard) to calculate amount (A), i.e., the amount of [$^{33}$P]-S1P binding to the membrane fraction in the presence of the compound.

The same procedure was performed in the absence of any test compound to calculate amount (B), i.e., the amount of [$^{33}$P]-S1P binding. Moreover, the same procedure was also performed with HEK-293 cells carrying no Edg-1($S1P_1$) gene in the absence of any test compound to calculate amount (C), i.e., the amount of background [$^{33}$P]-S1P binding.

The inhibition rate of Edg-1($S1P_1$) binding was calculated for each compound by the following equation.

$$\text{Inhibition rate (\%)} = [1-(A-C)/(B-C)] \times 100$$

The compounds of Compound Nos. 1 to 62 were subjected to the above test. In each of the tested compounds, the inhibition rate of Edg-1($S1P_1$) binding was 3% or more upon addition of the compound at 10 μM.

Moreover, the activity of each test compound was calculated as a value ($IC_{50}$ value) showing 50% of the radioactivity obtained in the absence of any test compound. Namely, the above membrane system binding test was performed in the presence of a test compound at various concentrations to calculate an $IC_{50}$ value according to the dose-dependent inhibition curve analyzed with data analysis software, Origin (Lightstone Corp., Japan).

The results indicated that the compounds listed below had $IC_{50}$ values of 200 nM or less and showed strong binding inhibition rates:

Compounds 7, 11, 22 and 57.

Moreover, detailed $IC_{50}$ data are shown below for individual compounds (unit: nM):

Compound 3: 107; Compound 4: 121; Compound 13: 47; Compound 19: 66;

Compound 27: 51; Compound 28: 49; Compound 31: 35; Compound 48: 63; Compound 55: 126; and Compound 61: 33.

INDUSTRIAL APPLICABILITY

Since the compounds of the present invention are excellent Edg-1($S1P_1$) ligands, they are useful as therapeutic and/or prophylactic agents for autoimmune diseases such as Crohn's disease, irritable bowel syndrome, Sjogren's syndrome, multiple sclerosis and systemic lupus erythematosus, as well as other diseases such as rheumatoid arthritis, asthma, atopic dermatitis, rejection after organ transplantation, cancer, retinopathy, psoriasis, osteoarthritis, age-related macular degeneration, etc.

The invention claimed is:

1. A compound represented by formula (I) or a pharmaceutically acceptable salt thereof:

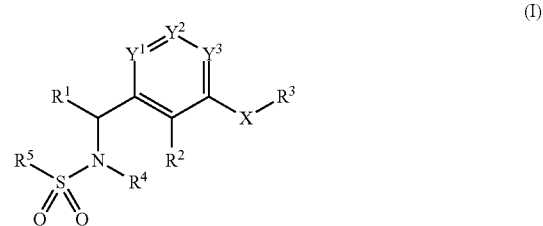

(I)

wherein $Y^1$ represents a nitrogen atom or a group represented by $CR^A$, $Y^2$ represents a nitrogen atom or a group represented by $CR^B$, $Y^3$ represents a nitrogen atom or a group represented by $CR^C$, provided that one of $Y^1$, $Y^2$ and $Y^3$ is nitrogen and the other two are carbon, $R^A$, $R^B$ and $R^C$, which may be the same or different, each represent a hydrogen atom or a $C_1$-$C_6$ alkyl group (excluding the case where $Y^1$ is $CR^A$, $Y^2$ is $CR^B$ and $Y^3$ is $CR^C$), X represents an oxygen atom, a sulfur atom, a group represented by the formula —SO—, a group represented by the formula —SO$_2$—, or a group represented by the formula —NR$^6$— (wherein $R^6$ represents a hydrogen atom or a $C_1$-$C_6$ alkyl group), $R^1$ represents a $C_1$-$C_6$ alkyl group, or a benzyl group, $R^2$ represents a hydrogen atom, a $C_1$-$C_6$ alkyl group, or a $C_3$-$C_8$ cycloalkyl group, $R^3$ represents (i) a $C_1$-$C_6$ alkyl group which may be substituted with 1 to 3 substituents selected from the group A [wherein the group A consists of a halogen atom, a phenyl group, a $C_1$-$C_6$ alkoxy group, an amino group which may be substituted with one or two $C_1$-$C_6$ alkyl groups, a morpholino group, and a piperazino group which may be substituted with a $C_1$-$C_6$ alkyl group(s)], (ii) a $C_3$-$C_8$ cycloalkyl group, or (iii) a phenyl group, a naphthyl group or an isoquinolinyl group, each of which may be substituted with 1 to 3 substituents selected from the group B [wherein the group B consists of a halogen atom, a $C_1$-$C_6$ alkyl group, a $C_1$-$C_6$ alkoxy group, an amino group which may be substituted with one or two $C_1$-$C_6$ alkyl groups, a morpholino group, a piperazino group which may be substituted with a $C_1$-$C_6$ alkyl group(s), a $C_1$-$C_6$ alkanoylamino group, and a $C_1$-$C_6$ alkylsulfonylamino group], $R^4$ represents a hydrogen atom or a $C_1$-$C_6$ alkyl group, and $R^5$ represents a phenyl group, a thienyl group, a thiazolyl group, a pyridyl group, a naphthyl group, an indanyl group, a dihydrobenzofuranyl group, a benzodioxolyl group, a benzothiadiazolyl group, a benzothienyl group or a quinolinyl group, each of which may be substituted with 1 to 5 substituents selected from the group C [wherein the group C consists of a $C_1$-$C_6$ alkyl group, a halogen atom, a trifluoromethyl group, a $C_1$-$C_6$ alkoxy group, a trifluoromethoxy group, a nitro group, a cyano group, and a $C_2$-$C_7$ alkanoyl group], or a $C_2$-$C_8$ alkenyl group which may be substituted with a phenyl group(s).

2. The compound or pharmaceutically acceptable salt thereof according to claim 1, wherein in formula (I), $Y^1$ is a nitrogen atom or CH, $Y^2$ is $CR^B$, and $Y^3$ is a nitrogen atom or CH.

3. The compound or pharmaceutically acceptable salt thereof according to claim 1, wherein in formula (I), $Y^1$ and $Y^2$ are each CH, and $Y^3$ is a nitrogen atom.

4. The compound or pharmaceutically acceptable salt thereof according to claim 1, wherein in formula (I), X is an oxygen atom.

5. The compound or pharmaceutically acceptable salt thereof according to claim 1, wherein in formula (I), $R^1$ is a $C_1$-$C_6$ alkyl group.

6. The compound or pharmaceutically acceptable salt thereof according to claim 1, wherein in formula (I), $R^1$ is a methyl group or an ethyl group.

7. The compound or pharmaceutically acceptable salt thereof according to claim 1, wherein in formula (I), $R^2$ is a hydrogen atom or a $C_1$-$C_6$ alkyl group.

8. The compound or pharmaceutically acceptable salt thereof according to claim 1, wherein in formula (I), $R^2$ is a methyl group or an ethyl group.

9. The compound or pharmaceutically acceptable salt thereof according to claim 1, wherein in formula (I), $R^4$ is a hydrogen atom.

10. The compound or pharmaceutically acceptable salt thereof according to claim 1, wherein in formula (I), $R^3$ is a phenyl group, a naphthyl group or an isoquinolinyl group, each of which may be substituted with 1 to 3 substituents selected from the group D [wherein the group D consists of a halogen atom, a $C_1$-$C_6$ alkyl group, a $C_1$-$C_6$ alkoxy group, an amino group which may be substituted with one or two $C_1$-$C_6$ alkyl groups, a morpholino group, and a piperazino group which may be substituted with a $C_1$-$C_6$ alkyl group(s)].

11. The compound or pharmaceutically acceptable salt thereof according to claim 1, wherein in formula (I), $R^3$ is a phenyl group whose meta position is substituted with one substituent selected from the group E [wherein the group E consists of an amino group which may be substituted with one or two $C_1$-$C_6$ alkyl groups, a morpholino group, and a piperazino group which may be substituted with a $C_1$-$C_6$ alkyl group(s)].

12. The compound or pharmaceutically acceptable salt thereof according to claim 1, wherein in formula (I), $R^5$ is a phenyl group, a thienyl group, a naphthyl group, a dihydrobenzofuranyl group, a benzodioxolyl group, a benzothiadiazolyl group, a benzothienyl group or a quinolinyl group, each of which may be substituted with 1 to 3 substituents selected from the group F [wherein the group F consists of a $C_1$-$C_6$ alkyl group, a halogen atom, a trifluoromethyl group, a $C_1$-$C_6$ alkoxy group, a nitro group, a cyano group, and a $C_2$-$C_7$ alkanoyl group], or a $C_2$-$C_8$ alkenyl group which may be substituted with a phenyl group(s).

13. The compound or pharmaceutically acceptable salt thereof according to claim 1, wherein in formula (I), $R^5$ is a phenyl group substituted with two or three halogen atoms or a naphthyl group substituted with one or two halogen atoms.

14. A pharmaceutical preparation comprising the compound or pharmaceutically acceptable salt thereof according to claim 1.

15. A method of treating an autoimmune disease selected from the group consisting of Crohn's disease, irritable bowel syndrome, Sjogren's syndrome, multiple sclerosis and systemic lupus erythematosus, or a disease selected from the group consisting of rheumatoid arthritis, asthma, atopic dermatitis, rejection after organ transplantation, retinopathy, psoriasis, osteoarthritis, and age-related macular degeneration, which comprises applying the compound or pharmaceutically acceptable salt thereof according to claim 1 to a patient in need thereof.

* * * * *